US012776399B2

(12) United States Patent
Zaidi et al.

(10) Patent No.: US 12,776,399 B2
(45) Date of Patent: Oct. 27, 2026

(54) ENHANCED ENTITY IDENTIFICATION FOR AUTOMATIC SOAP NOTE GENERATION

(71) Applicant: Oracle International Corporation, Redwood Shores, CA (US)

(72) Inventors: Syed Najam Abbas Zaidi, Melbourne (AU); Shiquan Yang, Melbourne (AU); Poorya Zaremoodi, Melbourne (AU); Nitika Mathur, Melbourne (AU); Shubham Pawankumar Shah, Foster City, CA (US); Arash Shamaei, Kirkland, WA (US); Sagar Kalyan Gollamudi, San Diego, CA (US)

(73) Assignee: Oracle International Corporation, Redwood Shores (CA)

( * ) Notice: Subject to any disclaimer, the term of this patent is extended or adjusted under 35 U.S.C. 154(b) by 0 days.

(21) Appl. No.: 18/883,595

(22) Filed: Sep. 12, 2024

(65) Prior Publication Data

US 2025/0095806 A1 Mar. 20, 2025

Related U.S. Application Data

(60) Provisional application No. 63/583,224, filed on Sep. 15, 2023.

(51) Int. Cl.
*G16H 10/60* (2018.01)
*G06F 40/205* (2020.01)
(Continued)

(52) U.S. Cl.
CPC ........... *G16H 10/60* (2018.01); *G06F 40/205* (2020.01); *G06F 40/295* (2020.01); *G06N 20/00* (2019.01);
(Continued)

(58) Field of Classification Search
None
See application file for complete search history.

(56) References Cited

U.S. PATENT DOCUMENTS

2019/0122766 A1* 4/2019 Strader ................. G06F 40/279
2022/0375605 A1* 11/2022 Lipton .................... G06F 40/30
(Continued)

OTHER PUBLICATIONS

Krishna et al. ("Generating SOAP Notes from Doctor-Patient Conversations Using Modular Summarization Techniques." In Proceedings of the 59th Annual Meeting of the Association for Computational Linguistics and the 11th International Joint Conference on Natural Language Processing, vol. 1, pp. 4958-4972 (Year: 2021).*

*Primary Examiner* — Christopher B Tokarczyk
(74) *Attorney, Agent, or Firm* — Kilpatrick Townsend & Stockton LLP

(57) ABSTRACT

Techniques are disclosed for automatically generating Subjective, Objective, Assessment and Plan (SOAP) notes. Particularly, techniques are disclosed for identifying entities for automatic SOAP note generation. A text transcript is accessed and segmented into portions. The text transcript can correspond to an interaction between a first entity and a second entity. Entities for the respective portions are identified using machine-learning models. A SOAP note is generated using the one or more machine-learning models and facts are derived from the text transcript based at least in-part on the entities. The SOAP note can be stored in a database in association with at least one of the first entity and the second entity.

20 Claims, 10 Drawing Sheets

(51) Int. Cl.

| | |
|---|---|
| ***G06F 40/295*** | (2020.01) |
| ***G06N 20/00*** | (2019.01) |
| ***G06N 20/20*** | (2019.01) |
| ***G10L 15/26*** | (2006.01) |
| ***G16H 10/00*** | (2018.01) |

(52) U.S. Cl.

CPC .............. *G06N 20/20* (2019.01); *G10L 15/26* (2013.01); *G16H 10/00* (2018.01)

(56) References Cited

U.S. PATENT DOCUMENTS

| | | | | |
|---|---|---|---|---|
| 2024/0127008 | A1* | 4/2024 | Pabolu | G06F 16/345 |
| 2025/0005282 | A1* | 1/2025 | Moriarty | G06F 16/345 |

* cited by examiner

ENHANCED ENTITY IDENTIFICATION FOR AUTOMATIC SOAP NOTE GENERATION

CROSS-REFERENCE TO RELATED APPLICATIONS

The present application claims the benefit of and priority to U.S. Provisional Application No. 63/583,224, filed Sep. 15, 2023, the entire contents of which are incorporated herein by reference for all purposes.

BACKGROUND

Clinical environments such as healthcare facilities often include different healthcare providers working together and communicating with one another to treat patients. Documenting patient encounters, capturing information conveyed during those encounters and/or pertaining to events occurring before and/or after the encounters, populating patient records such as electronic health records, and healthcare practice management are integral parts of the practice of many healthcare providers and important to ensuring high-quality healthcare. Traditional means for performing tasks associated with providing healthcare often involve several different devices such as listening devices, portable electronic devices, workstations, and the like and end users who are equipped with the training, knowledge, experience, and skills to properly utilize these devices and participate in the healthcare process. Relying on different devices and qualified end users to perform clinical tasks is cumbersome, time and resource intensive, costly, and reduces efficiencies, which may lead to lower-quality healthcare.

BRIEF SUMMARY

Techniques disclosed herein pertain to automatic Subjective, Objective, Assessment and Plan (SOAP) note generation. Particularly, techniques are disclosed herein for enhanced entity identification for automatic SOAP note generation.

In some embodiments, a computer-implemented method includes: accessing a text transcript, the text transcript corresponding to an interaction between a first entity and a second entity; segmenting the text transcript into a plurality of portions; for each respective portion of the plurality of portions: identifying one or more entities included in the respective portion, wherein identifying the one or more entities included in the respective portion includes: using a first machine-learning model to extract one or more first entities included in the respective portion, using a second machine-learning model to extract one or more second entities included in the respective portion, and combining the one or more first entities with the one or more second entities to result in the one or more entities; generating a Subjective, Objective, Assessment, and Plan (SOAP) note using a third machine-learning model based at least in-part on the one or more entities; and storing the SOAP note in a database associated with at least one of the first entity and the second entity.

In some embodiments, combining the one or more first entities with the one or more second entities to result in the one or more entities includes removing an entity included in the one or more second entities that are also included in the one or more first entities.

In some embodiments, combining the one or more first entities with the one or more second entities to result in the one or more entities includes comparing the one or more second entities to the respective portion to determine whether each second entity in the one or more second entities is included in the respective portion, and discarding any second entities in the one or more second entities that are not included in the respective portion.

In some embodiments, combining the one or more first entities with the one or more second entities to result in the one or more entities includes processing the one or more entities to remove additional instances of any entity that is included in the one or more entities more than once such that the one or more entities includes a single instance of each entity included in the one or more entities.

In some embodiments, the first machine-learning model is a named entity recognition model that is configured to recognize named entities in input text, wherein the second machine-learning model is a pre-trained language model that is configured to generate a result in response to an input prompt, and wherein the third machine-learning model is a pre-trained language model that is configured to generate a result in response to an input prompt.

In some embodiments, the method further includes: for each respective portion of the plurality of portions: using a fourth machine-learning model to extract one or more facts from the respective portion based at least in-part on the one or more entities, and adding the one or more facts to a collection of facts; and generating a set of classified facts from the collection of facts, wherein each classified fact of the set of classified facts corresponds to a fact in the collection of facts and is associated with a particular category label selected from a set of category labels.

In some embodiments, generating the SOAP note using the third machine-learning model based at least in-part on the one or more entities includes using the third machine-learning model to generate a set of note sections based at least in-part on the set of classified facts, wherein each note section of the set of note sections corresponds to a section of the SOAP note.

Some embodiments include a system that includes one or more processing systems and one or more computer-readable media storing instructions which, when executed by the one or more processing systems, cause the system to perform part or all of the operations and/or methods disclosed herein.

Some embodiments include one or more non-transitory computer-readable media storing instructions which, when executed by one or more processing systems, cause a system to perform part or all of the operations and/or methods disclosed herein.

The techniques described above and below may be implemented in a number of ways and in a number of contexts. Several example implementations and contexts are provided with reference to the following figures, as described below in more detail. However, the following implementations and contexts are but a few of many.

BRIEF DESCRIPTION OF THE DRAWINGS

Features, embodiments, and advantages of the present disclosure are better understood when the following Detailed Description is read with reference to the accompanying drawings.

DETAILED DESCRIPTION

Figure 1:
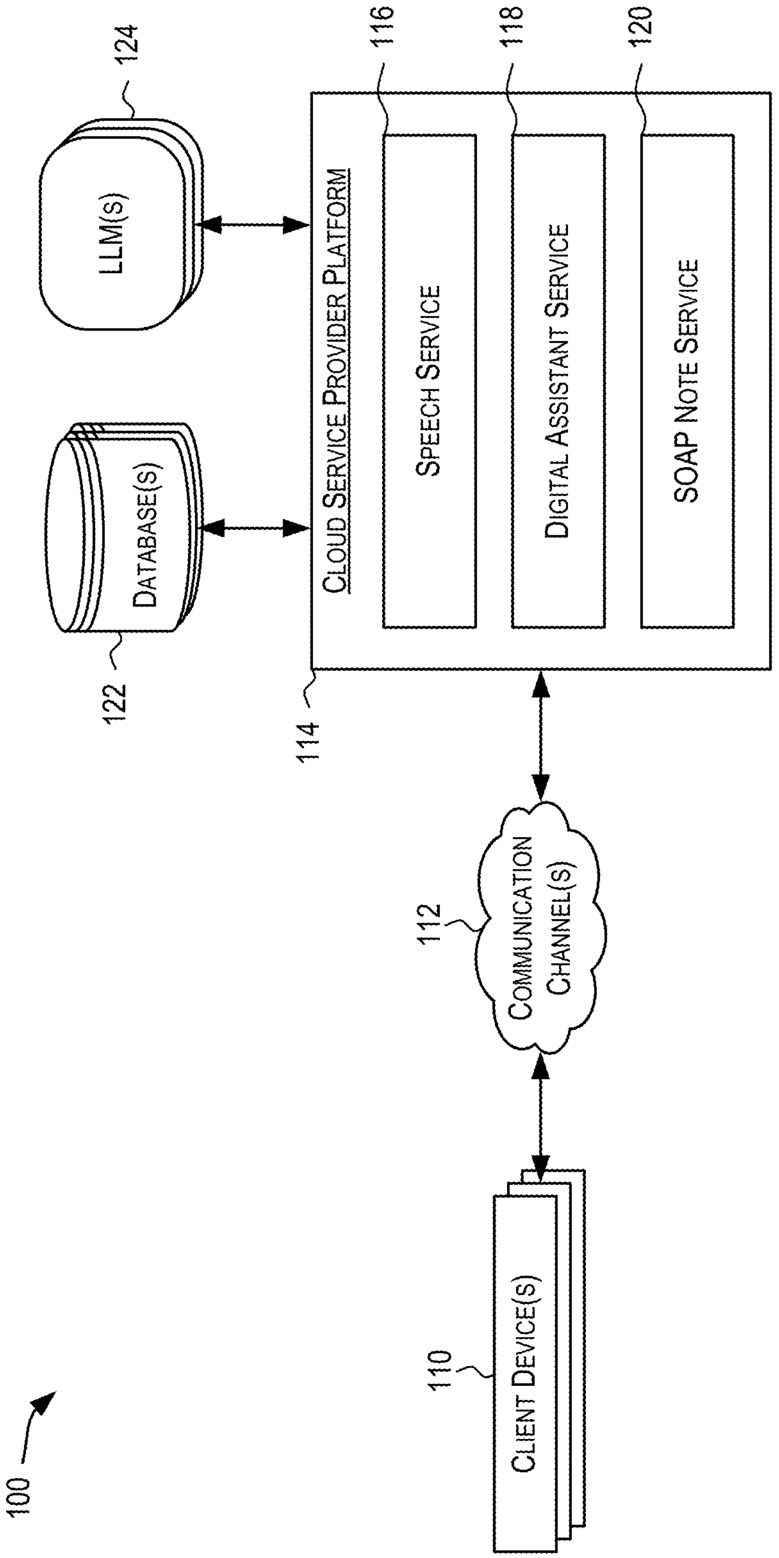
FIG. 1 is a simplified diagram of an example environment for automatically generating Subjective, Objective, Assessment and Plan (SOAP) notes, according to certain embodiments.

In the following description, for the purposes of explanation, specific details are set forth in order to provide a thorough understanding of certain embodiments. However, it will be apparent that various embodiments may be practiced without these specific details. The figures and description are not intended to be restrictive. The word "exemplary" is used herein to mean "serving as an example, instance, or illustration." Any embodiment or design described herein as "exemplary" is not necessarily to be construed as preferred or advantageous over other embodiments or designs.

INTRODUCTION

Healthcare providers often document encounters they have with patients. Documenting patient encounters is often an integral part of a healthcare provider's practice workflow that includes appointment scheduling, patient check-in and examination, patient treatment, billing, and the like. Additionally, documenting patient encounters assists healthcare providers in providing a cognitive framework for the healthcare providers to follow as they assess their patients during the encounters. The term healthcare provider generally refers to healthcare practitioners and professionals including, but not limited to: physicians (e.g., general practitioners, specialists, surgeons, etc.); nurse professionals (e.g., nurse practitioners, physician assistants, nursing staff, registered nurses, licensed practical nurses, etc.); and other professionals (e.g., pharmacists, therapists, technicians, technologists, pathologists, dietitians, nutritionists, emergency medical technicians, psychiatrists, psychologists, counselors, dentists, orthodontists, hygienists, etc.).

Healthcare providers often document patient encounters by generating notes that are structured and organized in a particular format. For example, a note documenting a patient encounter may start off by identifying the patient and listing the patient's physical characteristics (e.g., age, height, weight, eye color, hair color, etc.) and then may describe the patient's encounter with the healthcare provider (e.g., statements made, clinical information conveyed such as symptoms, problems, concerns, issues, treatments, prescribed medications, etc., additional information, and the like) and then they may provide concluding remarks (e.g., as abstract, a summary, other recommendations and information). Healthcare providers typically generate these notes in real-time (i.e., during the patient encounter) or just after the patient encounter and do so manually (i.e., handwritten) and/or using an electronic device (i.e., typewritten). In some cases, an assistant of the healthcare provider (e.g., a nurse) or a scribe will generate the note for the healthcare provider by observing or listening to the patient encounter and/or based on information acquired from other sources such as clinical records, healthcare provider notes, laboratory tests, and the like. Once a note is generated, it is typically stored in a record associated with the healthcare provider and/or the patient (e.g., an electronic healthcare management system of a healthcare provider, an electronic health record for the patient, and the like).

One example of a note used by healthcare providers for documenting patient encounters is a Subjective, Objective, Assessment and Plan (SOAP) note. SOAP notes provide healthcare providers with a structured, organized, and standardized format to document patient encounters, which facilitates the sharing of patient information in a clear, concise, universal, systematic, and easy-to-read way. Typically, a SOAP note can serve as a template for updating a patient's electronic health record after the patient's encounter with the healthcare provider. By using SOAP notes, healthcare providers seeking information regarding a patient can access SOAP notes generated based on previous encounters with the patient and readily understand a status of the patient and what occurred during the patient's previous encounters with the healthcare providers. Other benefits of using SOAP notes include facilitating better data integration and accessibility between healthcare systems, facilitating proper documentation and data-sharing practices, and reducing the risk of errors and omissions.

A SOAP note includes a Subjective component, an Objective component, and an Assessment and Plan component. The Subjective component (also referred to as the History of Present Illness or HPI component) is for documenting information pertaining to the patient. Such information can include, but is not limited to, the patient's complaints, symptoms, issues, concerns, history of illness, present illness, family medical and social history, current medications, previous medications, and the like. The Objective component (also referred to as the Review of Systems or ROS component) is for documenting information collected during the patient encounter such as vital signs, findings from a physical exam, results from diagnostic tests, and the like. Information documented by the Objective component can distinguish between symptoms and signs. The Assessment and Plan component is for summarizing the patient's condition including the patient's age, relevant medical history, a major diagnosis, and the patient's clinical stability and documenting the healthcare provider's differential diagnosis and proposed plan for addressing the patient's medical problems. This includes treatment plans, further diagnostic tests, referrals, and follow-up instructions. Table 1 shows an example of a SOAP note:

TABLE 1

| Patient: John Doe Age: 25 | Weight: 165 lbs |
|---|---|
| Subjective: | 25-year-old patient presents with a head contusion after falling from a horse onto a heavy wooden fence. Complains of head, neck, and knee pain, with a brief loss of consciousness observed by her brother. |

TABLE 1-continued

| Patient: John Doe | Age: 25 | Weight: 165 lbs |
|---|---|---|
| Objective: | Patient in no acute distress, stable with C-collar. Minimal tears in the occipital area, pupils equal and reactive. No blood in ears, tenderness over mid C-spine without swelling or deformity. Normal chest and abdominal exam, mild tenderness over right patella. | |
| Assessment and Plan: | Mild concussion. CT of the head after C-spine clearance. Home with head injury instructions. Follow-up in 12 days or return if any change in mental status. | |

Healthcare providers often practice healthcare in a broad range of clinical environments (e.g., hospitals, physician office's, patient's home, etc.) with different patient care objectives, and a typical healthcare provider-patient encounter can vary in terms of the number of dialogue turns, with some encounters being as short as ~50 dialogue turns and others being as long as ~200 dialogue turns. SOAP note generation is a complex task and, for a SOAP note to be effective and suitable for its intended purpose, the person or entity writing the SOAP note should be able disregard non-medically relevant information conveyed during the patient encounter, understand, contextually track, and summarize medical information conveyed during the patient encounter, and organize the summarized medical information into the structure and format of a SOAP note. SOAP notes are often generated manually (i.e., handwritten, typewritten, or a combination thereof) by multiple entities that are present during the patient encounter with each entity serving essentially as a scribe that listens to and observes the patient encounter and documents one or more aspects of the patient encounter for inclusion in a respective section of the SOAP note. As such, SOAP notes often differ in terms of style, format, consistency, writing level, grammar, readability, and the like, which can reduce their effectiveness and the benefits provided by SOAP notes.

Traditional means for overcoming the foregoing challenges have relied on machine-learning techniques to automatically generate a SOAP note or portions thereof from an audio recording of a healthcare provider-patient encounter and other information pertaining to the encounter. However, these traditional means are often prone to errors and instability due to the quality of the information being collected during the patient encounter and lack of readily available, low-cost training data. Some other traditional means for overcoming the foregoing challenges have used pre-trained language models such as large language models (LLMs) to automate one or more tasks involved in generating a SOAP note. However, these pre-trained language models are often costly to license and operate, lack the healthcare privacy safeguards expected by custom, law, regulation, and are poor at recognizing medical information, especially numerical information such as a medication and medication amount. In some cases, open-source pre-trained language models can be used, which can reduce costs and facilitate maintaining health privacy standards, but these models often have input window token limits, are inconsistent in performance, do not follow SOAP note structure, and are error prone (e.g., hallucinate, use incorrect terminology, and overlook important facts, numerical information, important entities, and other important details, and the like).

The techniques disclosed herein overcome the foregoing challenges and others by providing improved techniques for automatically generating SOAP notes using one or more machine-learning models and, particularly, to techniques for enhanced entity identification for automatic SOAP note generation. By providing enhanced entity identification techniques, fact extraction can be improved by focusing attention on particular portions of an interaction. By improving fact extraction, higher-quality SOAP notes can be automatically generated, which reduces the need for manual review of a generated SOAP note (e.g., by a medical professional or scribe) and improves quality levels of individual portions of the SOAP note. As such, high-quality SOAP notes can automatically be generated which can lead to higher-quality healthcare without incurring additional costs in terms of time, healthcare privacy, and financial resources.

In various embodiments, a computer-implemented method includes: accessing a text transcript, the text transcript corresponding to an interaction between a first entity and a second entity; segmenting the text transcript into a plurality of portions; for each respective portion of the plurality of portions: identifying one or more entities included in the respective portion, wherein identifying the one or more entities included in the respective portion includes: using a first machine-learning model to extract one or more first entities included in the respective portion, using a second machine-learning model to extract one or more second entities included in the respective portion, and combining the one or more first entities with the one or more second entities to result in the one or more entities; generating a SOAP note using a third machine-learning model based at least in-part on the one or more entities; and storing the SOAP note in a database associated with at least one of the first entity and the second entity.

As used herein, when an action is "based on" something, this means the action is based at least in part on at least a part of the something. As used herein, the terms "similarly," "substantially," "approximately" and "about" are defined as being largely but not necessarily wholly what is specified (and include wholly what is specified) as understood by one of ordinary skill in the art. In any disclosed embodiment, the term "similarly," "substantially," "approximately," or "about" may be substituted with "within [a percentage] of" what is specified, where the percentage includes 0.1, 1, 5, and 7 percent.

Overview

FIG. 1 shows a simplified diagram of an example environment for automatically generating SOAP notes. As shown in FIG. 1, the environment 100 includes one or more client devices 110 (hereinafter "client devices 110"), one or more communication channels 112 (hereinafter "communication channels"), a cloud service provider platform 114 (hereinafter "platform 114"), one or more databases 122 (hereinafter "databases 122"), and one or more LLMs 124 (hereinafter "LLMs"). The platform 114, which can be included as part of a cloud infrastructure of a cloud service provider (e.g., Oracle Cloud Infrastructure or OCI), can be configured to communicate with, send data and information to, and receive data and information from the client devices 110 via the communication channels 112. Additionally, the platform 114 can be configured to access and/or call the databases 122 and the LLMs 124 to obtain and/or receive data and information from the databases 122 and the LLMs 124. Data and information received from the client devices 110, the databases 122, and the LLMs 124 can be used by the platform 114 to execute tasks and perform services such as automatically generating SOAP notes. While FIG. 1 shows the databases 122 and the LLMs 124 as being separate from the platform 114, this is not intended to be limiting, and one or more of the databases 122 and/or one or more of the LLMs 124 can be included as part of the platform 114 and/or the cloud infrastructure in which the platform 114 is included.

Each client device included in the client devices 110 can be any kind of electronic device that is capable of: executing applications; presenting information textually, graphically, and audibly such as via a display and a speaker; collecting information via one or more sensing elements such as image sensors, microphones, tactile sensors, touchscreen displays, and the like; connecting to a communication channel such as the communication channels 112 or a network such as a wireless network, wired network, a public network, a private network, and the like, to send and receive data and information; and/or storing data and information locally in one or more storage mediums of the electronic device and/or in one or more locations that are remote from the electronic device such as a cloud-based storage system, the platform 114, and/or the databases 122. Examples of electronic devices include, but are not limited to, mobile phones, desktop computers, portable computing devices, computers, workstations, laptop computers, tablet computers, and the like.

In some implementations, an application can be installed on, executing on, and/or accessed by a client device included in the client devices 110. The application and/or a user interface of the application can be utilized and/or interacted with (e.g., by an end user) to access, utilize, and/or interact with one or more services provided by the platform 114. The client device can be configured to receive multiple forms of input such as touch, text, voice, and the like, and the application can be configured to transform that input into one or more messages which can be transmitted or streamed to the platform 114 using one or more communication channels of the communication channels 112. Additionally, the client device can be configured to receive messages, data, and information from the platform 114 using one or more communication channels of the communication channels 112 and the application can be configured to present and/or render the received messages, data, and information in one or more user interfaces of the application.

Each communication channel included in the communication channels 112 can be any kind of communication channel that is capable of facilitating communication and the transfer of data and/or information between one or more entities such as the client devices 110, the platform 114, the databases 122, and the LLMs 124. Examples of communication channels include, but are not limited to, public networks, private networks, the Internet, wireless networks, wired networks, fiber optic networks, local area networks, wide area networks, and the like. The communication channels 112 can be configured to facilitate data and/or information streaming between and among the one or more entities. In some implementations, data and/or information can be streamed using one or more messages and according to one or more protocols. Each of the one or more messages can be a variable length message and each communication channel included in the communication channels 112 can include a stream orchestration layer that can receive the variable length message in accordance with a predefined interface, such as an interface defined using an interface description language like AsyncAPI. Each of the variable length messages can include context information that can be used to determine the route or routes for the variable length message as well as a text or binary payload of arbitrary length. Each of the routes can be configured using a polyglot stream orchestration language that is agnostic to the details of the underlying implementation of the routing tasks and destinations.

Each database included in the databases 122 can be any kind of database that is capable of storing data and/or information and managing data and/or information. Data and/or information stored by each database can include data and/or information generated by, provided by, and/or otherwise obtained by the platform 114. Additionally, or alternatively, data and/or information stored and/or managed by each database can include data and/or information generated by, provided by, and/or otherwise obtained by other sources such as the client devices 110 and/or LLMs 124. One or more databases that are included in the databases 122 can be part of a platform for storing and managing healthcare information such as electronic health records for patients, electronic records of healthcare providers, and the like, and can store and manage electronic health records for patients of healthcare providers. An example platform is the Oracle Health Millenium Platform. Additionally, one or more databases included in the databases 122 can be provided by, managed by, and/or otherwise included as part of a cloud infrastructure of a cloud service provider (e.g., Oracle Cloud Infrastructure or OCI). Data and/or information stored and/or managed by the databases 122 can be accessed using one or more application programming interfaces (APIs) of the databases 122.

Each LLM included in the LLMs 124 can be any kind of LLM that is capable of obtaining or generating or retrieving one or more results in response to one or more inputs such as one or more prompts. Prompts for obtaining or generating or retrieving results from the LLMs 124 can obtained from or generated by or retrieved from or accessed from the client devices 110, the databases 112, the platform 114, and/or one or more other sources such as the Internet. Each prompt can be configured to cause the LLMs 124 to perform one or more tasks, which causes one or more results to be provided or generated and the like. Prompts for the LLMs 124 can be pre-generated (i.e., before they are needed for a particular task) and/or generated in real-time (i.e., as they are needed for a particular task). In some implementations, prompts for the LLMs 124 can be engineered to achieve a desired result or results manually and/or by one or more machine-learning models. In some implementations, prompts for the LLMs 124 can be engineered one demand (i.e., in real-time and/or as needed) and/or at particular intervals (e.g., once per day, upon log in by authenticated user into the platform 114). Each prompt of the one or more prompts can include a request for or a query for or a task to be performed by the LLMs 124 and contextual information. The contextual information can include information such as a text transcript or portions or segments thereof, information about an entity (e.g., information about a healthcare provider, information about a patient such as information included in an electronic health record for the patient, and the like), and/or other information or records (e.g., lab results, ambient temperature, and the like). LLMs included in the LLMs 124 can be pre-trained, fine-tuned, open source, off-the-shelf, licensed, subscribed to, and the like. Additionally, LLMs included in the LLMs 124 can include or have any size context window (i.e., can accept any number of tokens) and can be capable of interpreting complex instructions. One or more LLMs included in the LLMs 124 can be provided by, managed by, and/or otherwise included as part of the platform 114 and/or a cloud infrastructure of a cloud service provider (e.g., Oracle Cloud Infrastructure or OCI) that supports the platform 114. One or more LLMs included in the LLMs 124 can be accessed using one or more APIs of the LLMs 124 and/or a platform hosting or supporting or providing the LLMs 124.

The platform 114 can be configured to include various capabilities and provide various services to subscribers (e.g., end users) of the various services. In some implementations, in the case of an end user or subscriber being a healthcare provider, the healthcare provider can utilize the various services to facilitate the observation, care, treatment, management, and so on of their patient populations. For example, a healthcare provider can utilize the functionality provided by the various services provided by the platform 114 to examine and/or treat and/or facilitate the examination and/or treatment of a patient; view, edit, and/or manage a patient's electronic health record; perform administrative tasks such as scheduling appointments, managing patient populations, providing customer service to facilitate operation of a healthcare environment in which the healthcare provider practices, and so on.

In some implementations, the services provided by the platform 114 can include, but are not limited to, a speech service 116, a digital assistant service 118, and a SOAP note service 120. The speech service 116 can be configured to convert audio into text such as a text transcript. For example, the speech service 116 can convert an audio recording of a conversation between a healthcare provider and a patient into a text transcript of the conversation. To convert audio into text, the speech service 116 can utilize one or more machine-learning models such as an automatic speech recognition (ASR) model. In the case that the audio is streamed to the platform 114 in the form of messages (as described above) with each message including a portion of the audio (e.g., a one second segment of the audio), in some implementations, the platform 114 and/or the speech service 116 can be configured to aggregate and combine all of the messages pertaining to the audio (e.g., all of the messages pertaining to a conversation) into audio data and/or an audio file prior to converting the audio data or audio file into text and/or a text transcript. In other implementations, the platform 114 and/or the speech service 116 can be configured to convert audio into text or a text transcript as the audio is received by the platform 114 and/or the speech service 116. The text or text transcript generated by the speech service 116 can be stored within the platform 114 and/or in another location such as in one or more databases of the databases 122, where it can be accessed by the platform 114, one or more other services of the platform 114 such as the digital assistant service 118 and/or the SOAP note service 120, and/or the LLMs 124. Additionally, or alternatively, the text or text transcript generated by the speech service 116 can be provided to one or more other services of the platform 114 such as the digital assistant service 118 and/or the SOAP note service 120, and/or the LLMs 124.

The digital assistant service 118 can be configured to serve as an artificial intelligence-driven (AI-driven) conversational-type interface for the platform 114 that can conduct conversations with end users (e.g., those using the client devices 110) and perform functions and/or tasks based on the information conveyed by and/or ascertained from those conversations and other sources. The digital assistant service 118 can be configured with and/or configured to access natural language understanding (NLU) capabilities such as natural language processing, named entity recognition, intent classification, and so on. In some implementations, the digital assistant service 118 can be skill-driven in which the digital assistant service 118 includes bots that each include one or more skills for conducting conversations and performing functions and/or tasks. In some implementations, the digital assistant service 118 can be LLM-based and agent-driven in which agent(s) coordinate with LLM(s) for conducting conversations and performing functions and/or tasks. Examples of skill-driven and LLM-based and agent-driven digital assistants are described in U.S. Pat. No. 17,648,376, filed on Jan. 19, 2022, and U.S. patent application Ser. No. 18/624,472, filed on Apr. 2, 2024, each of which are incorporated by reference as if fully set forth herein.

The digital assistant service 118 can be configured to initiate a dialog, drive a previously initiated dialog (e.g., by responding to a turn in the dialog), and/or otherwise participate in a conversation. In some implementations, the digital assistant service 118 can drive and/or participate in a dialog and/or conversation in response to events that have occurred at the client devices 110, the platform 114, the databases 122, the LLMs 124, and/or at the cloud infrastructure supporting the platform 114. In the case of a skill-driven digital assistant service 118, the events can be mapped to a particular skill and can trigger a flow for that skill. The flow can then generate response events/messages that can be used to render a user interface such as a user interface of a client application executing on the client devices 110. In the case of an LLM-based and agent-drive digital assistant service 118, the events can be mapped to a particular prompt or prompts to retrieve a result or results for the prompt or prompts, which can then be used to render the user interface. In some implementations, the digital assistant service 118 can drive and/or participate in a dialog and/or conversation in response to messages received from the client devices 110, the platform 114, the databases 122, the LLMs 124, and/or at the cloud infrastructure supporting the platform 114. In the case of a skill-driven digital assistant service 118, the messages can be routed to a particular skill, which, as described above, can generate response events/messages for rendering the user interface. In the case of an LLM-based and agent-driven digital assistant service 118, the metadata included in the messages can be used to generate and/or access a particular prompt or prompts to retrieve a result and/or results that can be used to render the user interface.

The SOAP note service 120 can be configured to automatically generate SOAP notes. To generate a SOAP note, the SOAP note service 120 can be configured to access a text transcript and generate a SOAP note from the text transcript. The text transcript can be a text transcript generated by the speech service 116 from an audio recording and/or a text transcript stored in and/or accessed from the platform 114, the databases 122, the LLMs 124, and/or another location such as the client devices 110. The text transcript can correspond to an interaction between a first entity (e.g., a healthcare provider) and a second entity (e.g., a patient). In some implementations, the text transcript can correspond to an interaction between the first entity, the second entity, and one or more additional entities. The text transcript can be stored in a database or storage medium in association with the first entity, the second entity, and/or other entities. For example, the text transcript can be stored in a database of the databases 122 in association with an electronic record or electronic records of the healthcare provider and/or an electronic health record or electronic health records of a patient of the healthcare provider. In some implementations, the text transcript can be derived from an audio recording of the interaction using, for example, a machine-learning model such as an ASR model of the speech service 116. In some implementations, audio corresponding to an interaction between the first entity and the second entity can be recorded using an electronic device (e.g., a client device of the client devices 110), transmitted to the platform 114 via communications channel 112, and converted to a text transcript by the speech service 116. In some implementations, the audio recording can be of any length and can be recorded as part of a process for generating a SOAP note. In some implementations, to generate a SOAP note, the platform 114 can trigger the client devices 110 to record audio and send that recorded audio to the platform 114 and/or the databases 122, and the SOAP note service 120 can call the speech service 116 to generate a text transcript of the recorded audio and generate a SOAP note using the text transcript or portions or segments thereof. Similarly, in some implementations, to generate a SOAP note, the client devices 110 can record audio and send that recorded audio to the platform 114 and/or the databases 122 where the speech service 116 can receive and/or access that recorded audio, generate a text transcript, and provide the text transcript to the databases 122 and/or the SOAP note service 120 where it can be used to generate a SOAP note.

In some implementations, a SOAP note can be generated automatically in response to a particular trigger or indication. For example, an end user of the client devices 110 can provide an indication to the client devices 110 that a SOAP note is desired (e.g., a voice command), the client devices 110 can provide a message describing that indication to the platform 114 and/or the digital assistant 118, and the platform 114 and/or digital assistant 118 can call one or more services of the platform 114 such as the speech service 116 and the SOAP note service 120 to begin a process for generating a SOAP note. In another example, a conversation in which the digital assistant service 118 is a participant can learn that an end user intends for a SOAP note to be generated and can call the SOAP note service 120 to begin a process for a generating a SOAP note. In another example, a button in a graphical user interface displayed on the client devices 110 can be activated and cause the platform 114 and/or a service of the platform 114 to begin a process for generating a SOAP note. In another example, the speech service 116 can alert the digital assistant service 118 and/or the SOAP note service 120 that a text transcript is available and the digital assistant service 118 and/or the SOAP note service 120 can access the text transcript and begin a process for generating a SOAP note. In some implementations, a SOAP note can be generated automatically at particular intervals (e.g., once per day, every time an interaction between entities concludes, and the like).

The SOAP note service 120 can generate a SOAP note from the text transcript using the LLMs 124. To generate the SOAP from the text transcript using the LLMs 124, the SOAP note service 120 can access one or more prompts (e.g., one or more prompts stored in the platform 114, the databases 112, and/or in another location), and provide the one or more prompts to the LLMs 124 to obtain one or more results (hereinafter "results"). Each prompt of the one or more prompts can include a request for or a query for or a task to be performed by the LLMs 124 and contextual information. The contextual information can include the text transcript or portions or segments of the text transcript, information about an entity of the interaction (e.g., information about the healthcare provider, information about the patient such as information included in an electronic health record for the patient, and the like), and/or other information or records (e.g., lab results, ambient temperature, and the like). The results can include the SOAP note and/or portions or sections of the SOAP note that are combined or assembled into the SOAP note (e.g., by LLMs 124 or other processing). In some implementations, the results can be processed to refine the results. For example, the one or more prompts can include a prompt which when provided to the LLMs 124 causes the LLMs 124 to process the SOAP note to refine and/or improve the SOAP note in the case the results include the SOAP note and/or process the portions or sections of the SOAP note to refine and/or improve the portions or sections in case the results include the portions or sections of the SOAP note.

In some implementations, the SOAP note can be generated as a single task in which providing the one or more prompts to the LLMs 124 causes the LLMs 124 to generate SOAP note in a single step. In some implementations, because the one or prompts may be longer than a suitable context window of the LLMs 124 and/or include complex instructions for the LLMs 124, the single task can be decomposed into multiple sub-tasks. In some implementations, the SOAP note can be generated using a task decomposition process in which one or more prompts are provided to the LLMs 124 to perform one or more sub-tasks of a SOAP note generation process (e.g., a prompt which causes the LLMs 124 to extract facts from the text transcript and a prompt which causes the LLMs 124 to generate a SOAP note from the text transcript and the facts). Additionally, the SOAP note can be generated using a mixture of LLMs selected from the LLMs 124 such that an LLM of the LLMs 124 that is used for one particular task or sub-task of the SOAP note generation process is different from an LLM of the LLMs 124 that is used for another particular task or sub-task of the SOAP note generation process. In this way, control over the SOAP generation process and/or stages and/or tasks of the SOAP note generation process can be exerted, which can result in higher-quality SOAP notes, reduce the need for manual review of a generate SOAP note (e.g., by a medical professional or scribe), and facilitate debugging and troubleshooting in the case a SOAP note is generated having a quality level that is less than a desired level. In some implementations, in the case of SOAP note generation using task decomposition, each sub-task can be tuned by selectively providing different prompts to the LLMs 124 to obtains results from the LLMs 124 that have suitable quality levels.

SOAP notes generated by the SOAP note service 120 can be stored within the platform 114 and/or in another location such as in one or more databases of the databases 122, where they can be accessed by the platform 114, one or more other services of the platform 114 such as the digital assistant service 118, and/or the LLMs 124. Additionally, or alternatively, SOAP notes generated by the SOAP note service 120 can be provided to one or more other services of the platform 114 such as the digital assistant service 118 and/or the LLMs 124. For example, the SOAP note service 120 can generate a SOAP note and provide the SOAP note to the digital assistant service 118 where it can be used in a conversation the digital assistant service 118 is participating in. SOAP notes generated by the SOAP note service can be stored in a database or storage medium in association with one or more entities of the interaction. For example, a SOAP note documenting an interaction involving a healthcare provider and a patient can be stored in a database of the databases 122 in association with or within an electronic record or electronic records of the healthcare provider and/or an electronic health record or electronic health records of the patient, where it can be accessed by the healthcare provider, the patient, another healthcare provider, and so on.

Although not shown, the platform 114 can include other capabilities and services such as authentication services, management services, task management services, notification services, and the like. The various capabilities and services of the platform 114 can be implemented utilizing one or more computing resources and/or servers of the platform 114 and provided by the platform 114 by way of subscriptions. Additionally, or alternatively, while FIG. 1 shows the services of the platform 114 as being separate services, one or more of the services can be combined with other services and/or be considered to be a sub-service of another service. For example, as shown in FIG. 2, in the environment 200, the SOAP note service 120 can be SOAP note sub-service 220, which can be a sub-service of or part of the digital assistant service 118.

Figure 2:
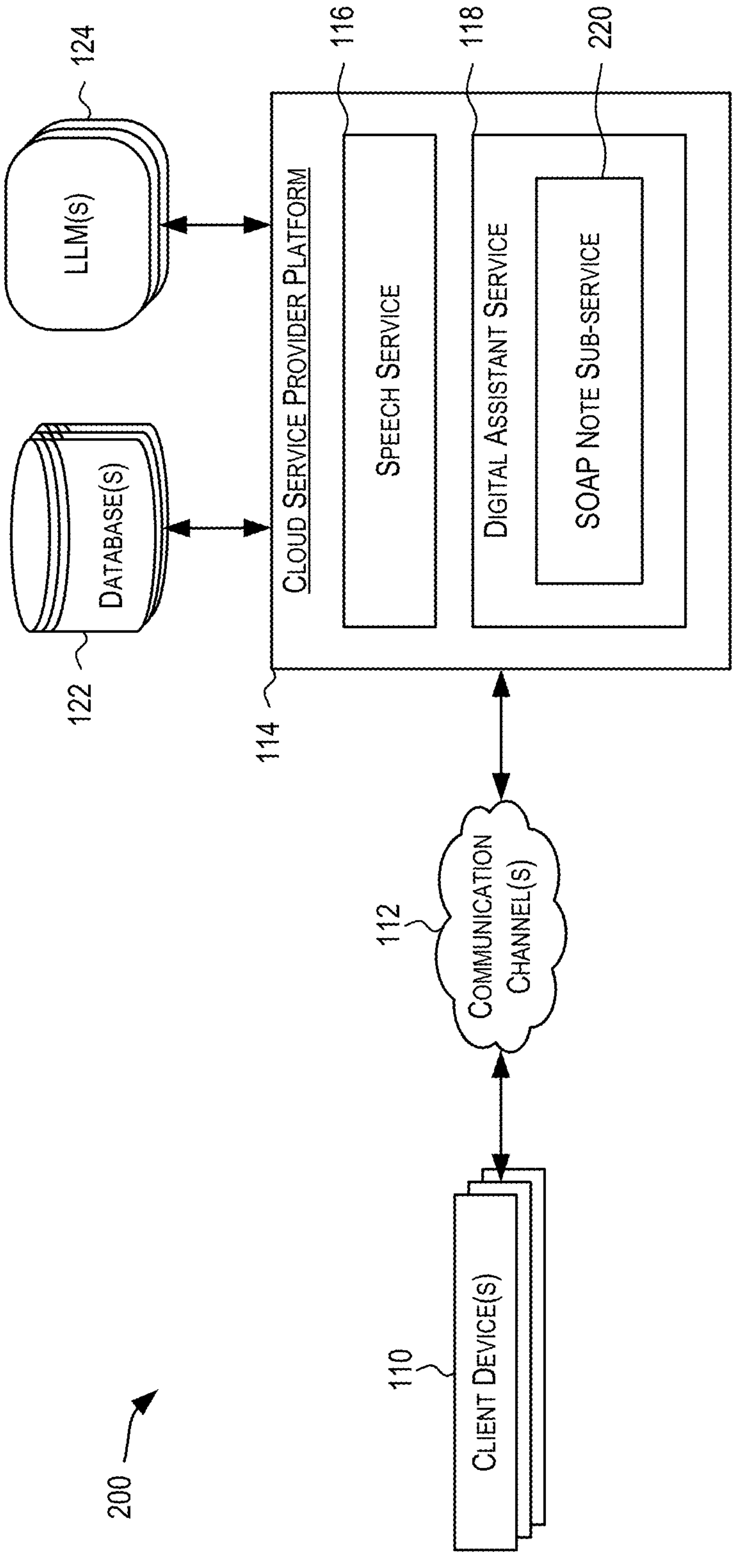
FIG. 2 is a simplified diagram of another example environment for automatically generating SOAP notes, according to certain embodiments.

The environments 100 and 200 depicted in FIGS. 1 and 2 are merely exemplary and are not intended to unduly limit the scope of claimed embodiments. One of ordinary skill in the art would recognize many possible variations, alternatives, and modifications. For example, in some implementations, the environments 100 and 200 can be implemented using more or fewer services than those shown in FIGS. 1 and 2, may combine two or more services, or may have a different configuration or arrangement of services.

Automatic SOAP Note Generation

Figure 3:
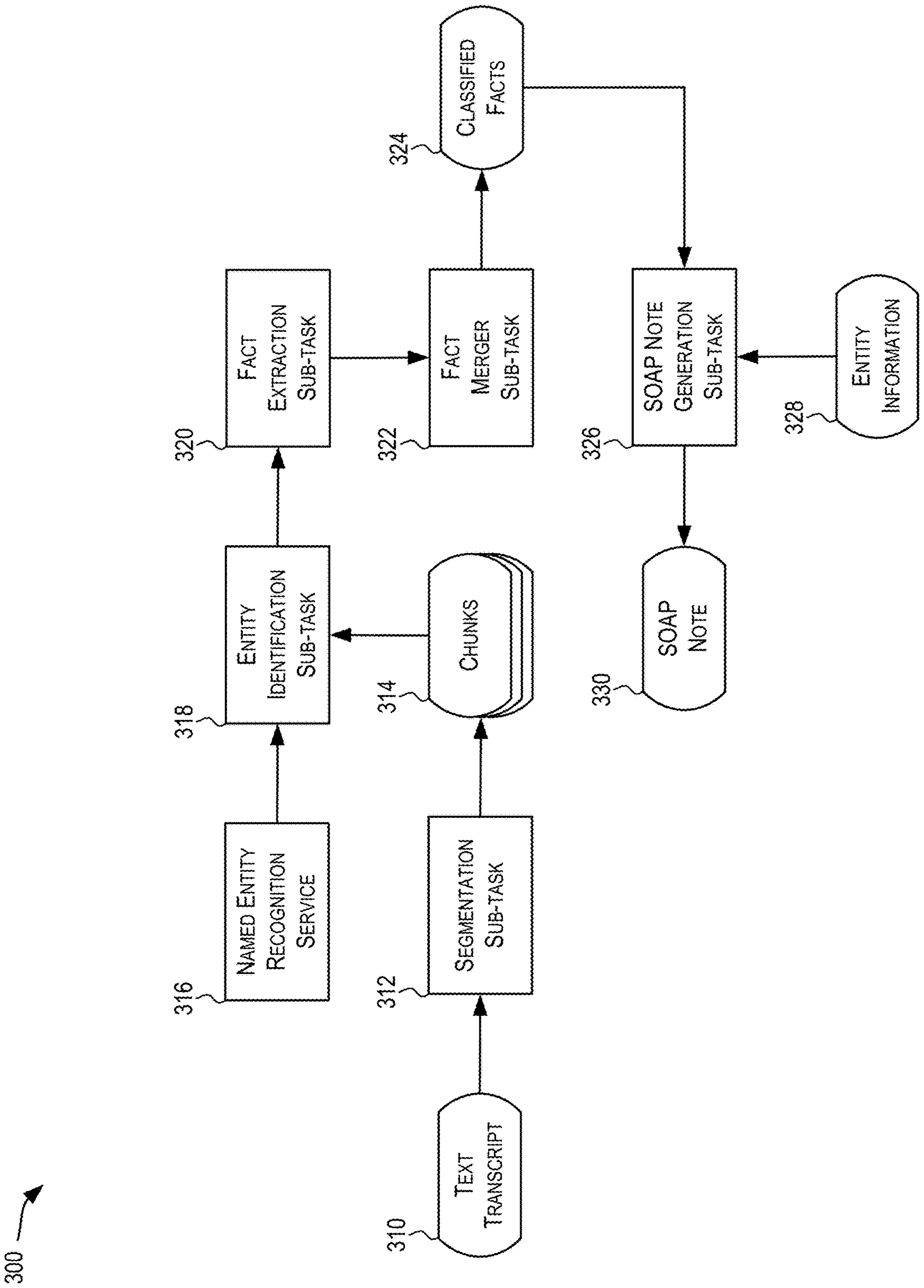
FIG. 3 depicts an example of a task flow for automatically generating a SOAP note, according to certain embodiments.

FIG. 3 depicts an example of a task flow 300 for automatically generating a SOAP note. As shown in FIG. 3, the task flow 300 includes a segmentation sub-task 312, an entity identification sub-task 318, a fact extraction sub-task 320, a fact merger sub-task 322, and a SOAP note generation sub-task 326. In some implementations, the task flow 300 is executed by a service of a cloud service provider platform such as the SOAP note service 120 of the platform 114.

The segmentation sub-task 312 is configured to segment a text transcript 310 into chunks 314. In some implementations, the text transcript 310 corresponds to an interaction between a first entity and a second entity. In some implementations, the text transcript is stored in the platform 114 and/or the databases 122. In some implementations, the first entity is a healthcare provider, the second entity is a patient associated with the healthcare provider, and the text transcript is stored in the platform and/or the database in association with an electronic record or electronic records of the healthcare provider and/or in association with and/or within an electronic health record or electronic health records of the patient of the healthcare provider. In some implementations, the text transcript 310 can be generated by converting audio into text. The audio can be an audio recording of the interaction between the first entity and the second entity. For example, an audio recording of a conversation between a healthcare provider and a patient can be converted into a text transcript of the conversation. To convert audio into a text transcript, one or more machine-learning models such as an ASR model can be utilized. The text transcript can be stored within the platform and/or the database, where it can be accessed and segmented into the chunks 314 by the segmentation sub-task 312.

The segmentation sub-task 312 can segment the text transcript 310 into equal sized chunks and/or variable sized chunks. For example, each chunk segmented at the segmentation sub-task 312 be the same size as each of the other chunks segmented at the segmentation sub-task 312. In another example, one or more chunks segmented at the segmentation sub-task 312 can be a different size than other chunks segmented at the segmentation sub-task 312. In some implementations, the text transcript 310 includes a first number of tokens and each chunk segmented at the segmentation sub-task 312 includes a second number of tokens that is less than the first number of tokens. In some implementations, segmenting the text transcript 310 into the chunks 314 includes selecting a respective portion of the text transcript 310 that has a number of tokens corresponding to the second number of tokens and determining whether the respective portion of the text transcript 310 satisfies predetermined criteria. In some implementations, the respective portion includes 250 tokens, which is less than the first number of tokens. In some implementations, the respective portion includes a sequence of turns of a dialog between the first entity and the second entity, where the sequence of turns includes a first turn, a last turn, and turns between the first turn and the last turn. In some implementations, determining whether the respective portion of the text transcript 310 satisfies the predetermined criteria includes determining whether the last turn of the sequence of turns includes a question or is an incomplete sentence. In some implementations, in response to determining that the last turn of the sequence of turns includes a question, a turn in the dialog from another portion of the text transcript 310 that answers the question is added to the respective portion such that the last turn of the sequence of turns in the modified respective portion is not a question and the modified respective portion is added to the chunks 314. In some implementations, in response to determining that the last turn of the sequence of turns is an incomplete sentence, a turn in the dialog from another portion of the plurality of portions is added to the respective portion such that the last turn of the sequence of turns of the modified respective portion is a complete sentence and the modified respective portion is added to the chunks 314.

The entity identification sub-task 318 is configured to identify one or more entities in each chunk of the chunks 314. In some implementations, the entity identification sub-task 318 is configured to identify one or more entities in each chunk of the chunks 314 using a machine-learning model and a machine-learning model prompt for the machine-learning model. In some implementations, the machine-learning model is an LLM. In some implementations, the LLM can be configured to identify medical or clinical or healthcare entities in the text of each respective chunk of the chunks 314. Examples of medical or clinical or healthcare entities include, but are not limited to, patients, doctors, medications, medication amounts, vital signs, test or examination or laboratory results, and the like. In some implementations, for each respective chunk of the chunks 314, a machine-learning model prompt is used to obtain results from the machine-learning model by providing the machine-learning model prompt to the machine-learning model as an input. The results can include a list (e.g., a comma separated list) or table of any entities included in the respective chunk (e.g., one entity, two entities, and so on). In some implementations, the results can be compared be to the respective chunk to determine whether any entities included in the results are not also included in the respective chunk. For example, a check can be made as whether tokens corresponding to each entity included in the results match any tokens in the respective chunk. In the case that an entity included in the results is not also included in the respective chunk, the entity can be removed from the results to result in filtered results. In some implementations, the machine-learning model prompt can include a query and context information. The query can be a query for extracting entities from the respective chunk (e.g., the query can be "Please extract all medically relevant entities of no more than 3 words from the conversation below and present them in a bullet list format."). The context information can include the respective chunk (e.g., the context information can include the text of the respective chunk). In some implementations, the machine-learning model prompt used at the entity identification sub-task 318 can be automatically engineered by the LLMs 124 and/or accessed from the platform 114, the databases 122, or another source such as the Internet.

In some implementations, the results or filtered results can be combined with results obtained from another machine-learning model and/or service that is configured to extract entities from text. In some implementations, a named entity recognition (NER) service 316 can be accessed and used to identify one or more entities in each chunk of the chunks 314. In some implementations, the NER service can include a machine-learning model (e.g., a NER model) that is configured to identify medical or clinical or healthcare entities in the text of each respective chunk of the chunks 314. In some implementations, for each respective chunk of the chunks 314, the respective chunk can be provided to the NER service 316 to obtain results from the NER service 316. The results can include a list (e.g., a comma separated list) of any entities included in the respective chunk. In some implementations, the results obtained from the NER service 316 can be combined with the results or filtered results obtained from the machine-learning model to result in merged results. The merged results can include a list (e.g., a comma separated list) or table of entities included in the respective chunk. In some implementations, the merged results can be processed to determine whether any entities and/or variations of any entities included in the merged results are duplicated and remove an instance(s) of the duplicated entity from the merged results such that the processed merged results include a single instance of the duplicated entity. For example, a check can be made as to whether tokens corresponding to each entity instance included in the merged results matches tokens corresponding to the other entity instances in the merged results. In the case that an entity included in the merged results is duplicated in the merged results, additional instances of the duplicated entity can be discarded such that the processed merged results include a single instance of the duplicated entity.

The fact extraction sub-task 320 is configured to extract one or more facts from each chunk of the chunks 314. In some implementations, the fact extraction sub-task 320 is configured to extract one or more facts from each chunk of the chunks 314 using a machine-learning model and a machine-learning model prompt for the machine-learning model. In some implementations, the machine-learning model is an LLM. In some implementations, the machine-learning model is the same as or different than the machine-learning model used at the entity identification sub-task 318. In some implementations, for each respective chunk of the chunks 314, a machine-learning model prompt is used to obtain results from the machine-learning model by providing the machine-learning model prompt to the machine-learning model as an input. The results can include a list (e.g., a comma separated list) or table of any facts included in the respective chunk (e.g., one fact, two facts, and so on). In some implementations, the machine-learning model prompt can include a query and context information. The query can be a query for extracting facts from the respective chunk (e.g., the query can be "Please generate an abstractive summary of the conversation below covering the mentioned entities. The summary should be suitable for physician's notes. Each line should mention whether it is stated by the doctor or the patient. Make sure to include important numbers if they are mentioned in the conversation."). The context information can include the results, the filtered results, or the merged results generated at the entity identification sub-task 318 and the respective chunk (e.g., the context information can include a list of entities extracted from the text of the respective chunk and the text of the respective chunk). The results generated for each respective chunk of the chunks 314 can be combined into a collection of facts for the chunks 314. For example, the collection of facts for the chunks 314 can include all the facts extracted for each of the respective chunks of the chunks 314. In some implementations, the machine-learning model prompt used at the fact extraction sub-task 320 can be automatically engineered by the LLMs 124 and/or accessed from the platform 114, the databases 122, or another source such as the Internet.

The fact merger sub-task 322 is configured to generate a set of classified facts 324 from the collection of facts. In some implementations, the fact merger sub-task 322 is configured to generate the set of classified facts 324 by classifying each fact included in the collection of facts and assigning a category label to each respective fact included in the collection of facts based on a class assigned to the respective fact by the classification. The category label assigned to a respective fact included in the collection of facts can be selected from a set of category labels based on the class assigned to the respective fact. Each category label included the set of category labels can correspond to or belong to a particular SOAP note section of a SOAP to be generated (i.e., the SOAP note to be generated by the task flow 300). For example, as described above, a SOAP note to be generated can include a subjective section, an objective section, and an assessment and plan section, and a category label included in the set of category labels can be associated with the subjective section, a category label included in the set of category labels can be associated with the objective section, and a category label included in the set of category labels can be associated with assessment and plan section. In this way, facts included in the collection of facts can be labeled as corresponding to or belonging to or being associated with a particular note section of a SOAP note.

The fact merger sub-task 322 is configured to classify each fact included in the collection of facts using a machine-learning model and a machine-learning model prompt for the machine-learning model. In some implementations, the machine-learning model is an LLM. In some implementations, the machine-learning model is the same as or different than the machine-learning model or models used at the entity identification sub-task 318 and the fact extraction sub-task 320. In some implementations, a machine-learning model prompt is used to obtain results from the machine-learning model by providing the machine-learning model prompt to the machine-learning model as an input. The results can include the collection of facts and category labels assigned to the facts included in collection of facts. In some implementations, each fact in the collection of facts can be assigned one or more category labels included in the set of category labels (e.g., one fact included in the collection of facts can be assigned a category label corresponding to or belonging to or associated with the subjective section of the SOAP note and a category label corresponding to or belonging to or associated with the objective section of the SOAP note).

The machine-learning model prompt for generating the set of classified facts can include a query and context information. The query can be a query for classifying facts in the collection of facts and assigning labels to the classified facts (e.g., the query can be "Please classify each of the facts in the following list of facts as corresponding to or belong to or being associated with a SOAP note section from among the following SOAP note sections. Please also assign a category label to each of the facts based on the classification of each of the facts. Each fact can have more than one category label. Please generate subset of facts organized by category label."). The context information can include the collection of facts and a list of SOAP note sections for the SOAP note that is to be generated. In some implementations, the machine-learning model prompt used at the fact merger sub-task 322 can be automatically engineered by the LLMs 124 and/or accessed from the platform 114, the databases 122, or another source such as the Internet.

In some implementations, prior to classifying facts in the collection of facts as corresponding to or belonging to or associated with a particular SOAP note section of the SOAP note to be generated, the fact merger sub-task 322 can be configured to generate a set of filtered facts by classifying each fact included in the collection of facts as being a medical fact or not being a medical fact. Examples of medical facts include, but are not limited to, facts pertaining to practice of medicine and/or treatment of illness and/or injuries. The fact merger sub-task 322 is configured to classify each fact included in the collection of facts as being a medical fact or not being a medical fact using a machine-learning model and a machine-learning model prompt for the machine-learning model. In some implementations, the machine-learning model is an LLM. In some implementations, the machine-learning model is the same as or different than the machine-learning model or models used in other sub-tasks of the task flow 300. In some implementations, a machine-learning model prompt is used to obtain results from the machine-learning model by providing the machine-learning model prompt to the machine-learning model as an input. The results can include a set of filtered facts in which each fact in the set of filtered facts is medically relevant. In some implementations, in the case the fact merger sub-task 322 generates a set of filtered facts prior to generating the set of classified facts, the context information of the machine-learning model prompt used to generate the set of classified facts can include the set of filtered facts (i.e., can include a set of medically relevant facts). In this way, medically relevant facts in the collection of facts can be labeled as corresponding to or belonging to or associated with a particular note section of a SOAP note.

The machine-learning model prompt for generating the set of filtered facts can include a query and context information. The query can be a query for classifying facts in the collection of facts and assigning labels to the classified facts (e.g., the query can be "Please classify and label each of the facts in the following list of facts as being medically relevant or not being medically relevant. Please generate a set of filtered facts based on the classification and labels."). The context information can include the collection of facts and examples of medically relevant facts. In some implementations, the machine-learning prompt for generating the set of filtered facts can be included in and/or combined with the machine-learning prompt for generating the set of classified facts such that providing the machine-learning model prompt to the machine-learning model prompt causes the machine-learning model to generate results that include a set of filtered and classified facts. In some implementations, the machine-learning prompt for generating the set of filtered facts can be provided to the machine-learning model before and/or after the machine-learning prompt for generating the set of classified facts is provided to the machine-learning model such that non-medically relevant facts in the collection of facts can be discarded prior to generating the SOAP note.

Any facts included the set of classified facts that have been assigned the subjective section category label (i.e., those that are classified are corresponding to or belonging to or associated with the subjective section of the SOAP note) can be organized into and/or otherwise included in a first subset of classified facts. Any facts in the set of classified facts that have been assigned the objective section category label (i.e., those that are classified are corresponding to or belonging to or associated with the objective section of the SOAP note) can be organized into and/or otherwise included in a second subset of classified facts. Any facts in the set of classified facts that include the assessment and plan section category label (i.e., those that are classified are corresponding to or belonging to or associated with the assessment and plan section of the SOAP note) can be organized and/or included in a third subset of classified facts.

Figure 4:
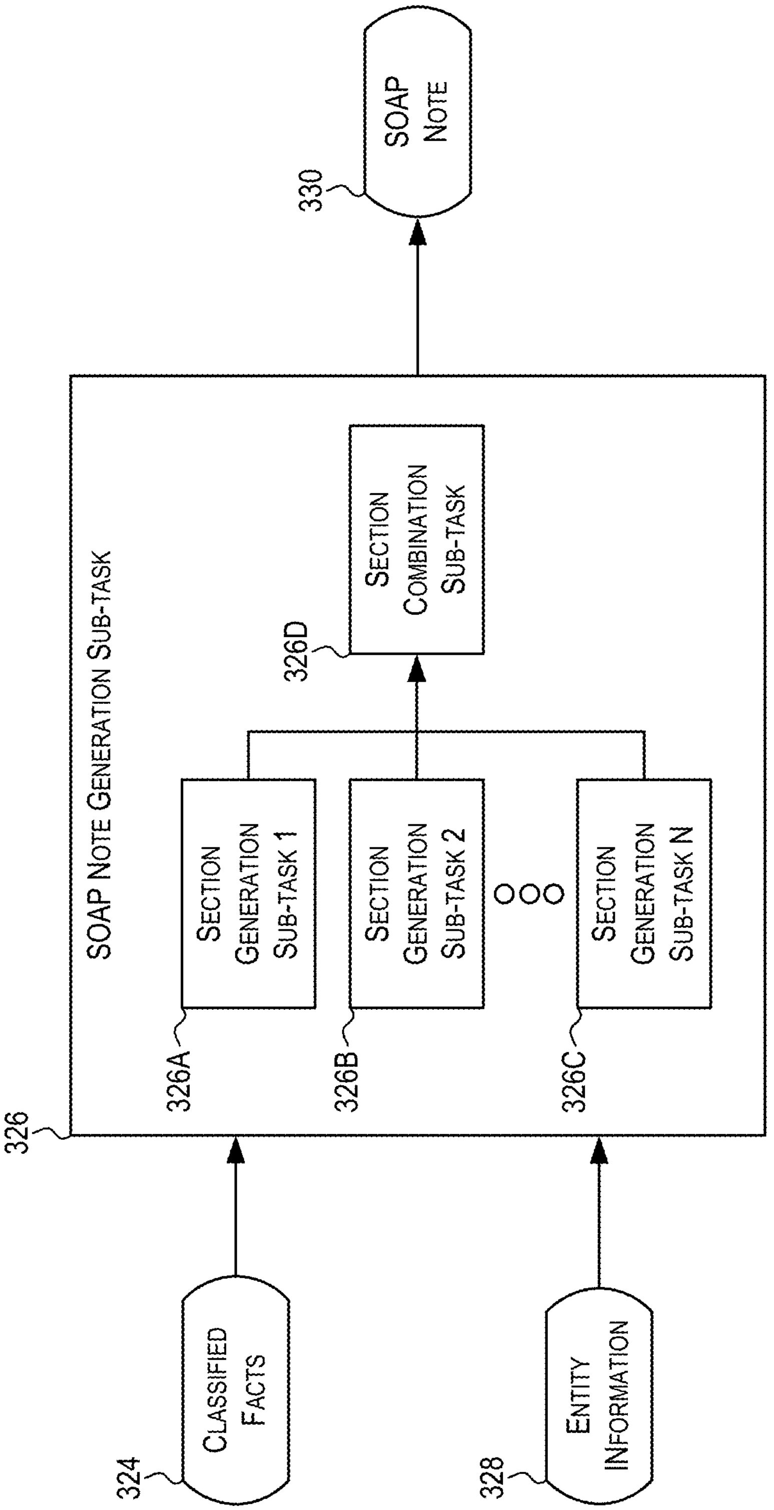
FIG. 4 depicts an example of a SOAP note generation task that includes sub-tasks, according to certain embodiments.

The SOAP note generation sub-task 326 is configured to generate a SOAP note 330 from the set of classified facts 324. In some implementations, the SOAP generation sub-task 326 is configured to generate the SOAP note 330 by generating SOAP note sections of the SOAP note 330 and combining the SOAP note sections into the SOAP note 330. In some implementations, the SOAP note generation sub-task 326 can include sub-tasks for generating the SOAP note sections of the SOAP note 330 and a sub-task for combining the SOAP note sections into the SOAP note 330. FIG. 4 depicts an example of a SOAP note generation task such as the SOAP note generation sub-task 326 that includes sub-tasks. The SOAP note generation sub-task 326 shown in FIG. 4 includes section generation sub-task 1 326A, section generation sub-task 2 326B, section generation sub-task N 326C, and so on, for generating SOAP note sections that are to be included in the SOAP note 330. The SOAP note generation sub-task 326 shown in FIG. 4 also includes a section combination sub-task 326D for combining the SOAP note sections generated by the section generation sub-tasks 1-N 326A-326C. Each section generation sub-task can be used to generate a particular SOAP note section of the SOAP note 330. For example, as described above, the SOAP note to be generated can include a subjective section (e.g., HPI component), an objective section (e.g., ROS component), and an assessment and plan section and the section generation sub-task 1 326A can used to generate the subjective section, the section generation sub-task 2 326B can be used to generate the objective section, and the section generation sub-task N 326C can be used to generate the assessment and plan section.

The section generation sub-task 1 326A is configured to generate a respective SOAP note section of the SOAP note 330 such as the HPI component using a machine-learning model and a machine-learning model prompt for the machine-learning model. In some implementations, the machine-learning model is an LLM. In some implementations, the machine-learning model is the same as or different than the machine-learning model or models used at other sub-tasks of the task flow 300. In some implementations, a machine-learning model prompt is used to obtain results from the machine-learning model by providing the machine-learning model prompt to the machine-learning model as an input. The results can include the respective SOAP note section. The respective SOAP note included in the results can be styled in a style and formatted in a format that corresponds to and/or matches the style and format of the SOAP note 330. The machine-learning model prompt for generating the respective SOAP note section can include a query and context information. The query can be a query for generating the respective SOAP note section and generating the respective SOAP note section in the style and format of the SOAP note 330. (e.g., the query to generate an HPI component of a SOAP note can be "Given the following list of facts derived from a doctor-patient conversation, write a History of Present Illness section of a SOAP note. Do not mention any information that doesn't appear in the list of facts. Please use a paragraph format and a continuous narrative."). The context information can include the facts included in the first subset of classified facts. For example, the context information can include the facts included in the set of classified facts that have been assigned the subjective section category label (i.e., those that are classified as corresponding to or belonging to or associated with the subjective section of the SOAP note). The context information can also include entity information 328 such as medical or healthcare information for the patient of the interaction (e.g., patient's age, gender, weight, and so on). The medical or health information can be derived from an electronic health record for the patient such as those described above and stored in the platform and/or database. In some implementations, the machine-learning model prompt used at the section generation sub-task 1 326A can be automatically engineered by the LLMs 124 and/or accessed from the platform 114, the databases 122, or another source such as the Internet.

The section generation sub-task 2 326B is configured to generate a respective SOAP note section of the SOAP note 330 such as the ROS component using a machine-learning model and a machine-learning model prompt for the machine-learning model. In some implementations, the machine-learning model is an LLM. In some implementations, the machine-learning model is the same as or different than the machine-learning model or models used at other sub-tasks of the task flow 300. In some implementations, a machine-learning model prompt is used to obtain results from the machine-learning model by providing the machine-learning model prompt to the machine-learning model as an input. The results can include the respective SOAP note section. The respective SOAP note included in the results can be styled in a style and formatted in a format that corresponds to and/or matches the style and format of the SOAP note 330. The machine-learning model prompt for generating the respective SOAP note section can include a query and context information. The query can be a query for generating the respective SOAP note section and generating the respective SOAP note section in the style and format of the SOAP note 330. (e.g., the query to generate an ROS component of a SOAP note can be "You are a scribe. Do the facts contain medical symptoms? If yes, please extract all the patient's medical symptoms related information that are suitable for the Review of Systems section of a SOAP note from the facts mentioned below. Follow the instructions below while extracting the symptoms: 1. Only extract the symptoms verbalized by the patient. 2. Do not add fluff in the extracted symptoms. 3. Please do not include psychological symptoms. 4. Provide output as none if no symptom exists in the notes. 5. Only extract the medical symptoms that are present in the notes. 6. Provide the output in a bulleted list format. 7. Focus on capturing negative symptoms too meaning the symptoms that have been negated but were still discussed in the facts. 8. Do not capture diagnosis or disease."). The context information can include the facts included in the second subset of classified facts. For example, the context information can include the facts included in the set of classified facts that have been assigned the objective section category label (i.e., those that are classified are corresponding to or belonging to or associated with the objective section of the SOAP note). The context information can also include entity information 328 such as medical or healthcare information for the patient of the interaction (e.g., patient's age, gender, weight, and so on). The medical or health information can be derived from an electronic health record for the patient such as those described above and stored in the platform and/or database. In some implementations, the machine-learning model prompt used at the section generation sub-task 2 326B can be automatically engineered by the LLMs 124 and/or accessed from the platform 114, the databases 122, or another source such as the Internet.

The section generation sub-task N 326C is configured to generate a respective SOAP note section of the SOAP note 330 such as the Assessment and Plan component using a machine-learning model and a machine-learning model prompt for the machine-learning model. In some implementations, the machine-learning model is an LLM. In some implementations, the machine-learning model is the same as or different than the machine-learning model or models used at other sub-tasks of the task flow 300. In some implementations, a machine-learning model prompt is used to obtain results from the machine-learning model by providing the machine-learning model prompt to the machine-learning model as an input. The results can include the respective SOAP note section. The respective SOAP note included in the results can be styled in a style and formatted in a format that corresponds to and/or matches the style and format of the SOAP note 330. The machine-learning model prompt for generating the respective SOAP note section can include a query and context information. The query can be a query for generating the respective SOAP note section and generating the respective SOAP note section in the style and format of the SOAP note 330. (e.g., the query to generate an Assessment and Plan component of a SOAP note can be: (i) "Generate the Assessment section of a SOAP note for the following list of facts derived from a doctor-patient conversation. The section should only include the doctor's diagnosis of the patient's problems. Do not include doctor suggestions about how to address the problems."; and (ii) "Generate the Plan section of a SOAP note for the following list of facts derived from the doctor-patient conversation."). The context information can include the facts included in the third subset of classified facts. For example, the context information can include the facts included in the set of classified facts that have been assigned the assessment and plan section category label (i.e., those that are classified are corresponding to or belonging to or associated with the assessment and plan section of the SOAP note). The context information can also include entity information 328 such as medical or healthcare information for the patient of the interaction (e.g., patient's age, gender, weight, and so on). The medical or health information can be derived from an electronic health record for the patient such as those described above and stored in the platform and/or database. In some implementations, the machine-learning model prompt used at the section generation sub-task N 326C can be automatically engineered by the LLMs 124 and/or accessed from the platform 114, the databases 122, or another source such as the Internet.

The section combining sub-task 326D is configured to combine the respective SOAP note sections generated by the section generation sub-task 1 326A, the section generation sub-task 2 326B, and the section generation sub-task N 326C into the SOAP note 330. The section combining sub-task 326D can generate the SOAP note 330 by accessing a SOAP note template (e.g., a template stored in the platform and/or the database and/or accessed from another source such as the Internet) and inserting the respective SOAP note sections into respective template sections of the SOAP note template. For example, a subjective section of the SOAP note would be inserted into a corresponding section in the SOAP note template, an objective section of the SOAP note would be inserted into a corresponding section in the SOAP note template, and an assessment and plan section of the SOAP note would be inserted into a corresponding section in the SOAP note template. In some implementation, the section combining sub-task 326D can generate the SOAP note 330 by generating a data structure and storing the respective SOAP note sections in the data structure.

The SOAP note generation sub-task 326 is configured to store the SOAP note 330 and the data structure that includes the SOAP note in the platform 114 and/or the databases 122 and/or send the SOAP note 330 and/or the data structure that includes the SOAP note to a remote location such as the client devices 110. In some implementations, the SOAP note 330 and/or the data structure that includes the SOAP note is stored in a database that is associated with at least one of the first entity and the second entity. In some implementations, the SOAP note 330 and/or the data structure that includes the SOAP note is stored in an electronic health record of the patient of the interaction. In this way, an automatically generated SOAP note that documents an encounter between a healthcare provider and a patient can be stored in the patient's electronic health record such that one or more other entities such as one or more other healthcare providers can access the SOAP note at a later time.

As described above, the machine-learning models used for the sub-tasks of the task flow 300 can be same machine-learning models. In some implementations, one or more of the machine-learning models used for one or more of the sub-tasks of the task flow 300 can be different from one or more machine-learning models used in one or more other sub-tasks of the task flow 300. In this way, a machine-learning model that performs well for one particular task can be used for that particular task and a machine-learning model that performs well for another particular task can be used for that particular task. In some implementations, prior to generating the SOAP note 300, a task can be performed to identify the machine-learning models to be used at the sub-tasks of the task flow 300. In some implementations, once a machine-learning model is identified for a particular sub-task, a machine-learning model prompt for that machine-learning model can be automatically engineered and/or accessed from a cloud service provider platform, database, another storage medium, and/or another source such as the Internet and can be used to obtain results from the machine-learning model. In this way, the task flow 300 can be decomposed into sub-tasks in which can be performed using machine-learning models that perform well for the respective sub-tasks. In some implementations, the machine-learning models can be evaluated in terms of performance such as frequency of hallucinations, output structure performance, repetition performance, and so on, and can be selected based in-part on their performances. While the techniques described herein have been described with respect to machine-learning models that accept a machine-learning model prompt as an input, this is not intended to be limiting, and machine-learning models that accept other forms of input may be used at the sub-tasks.

Illustrative Method

Figure 5:
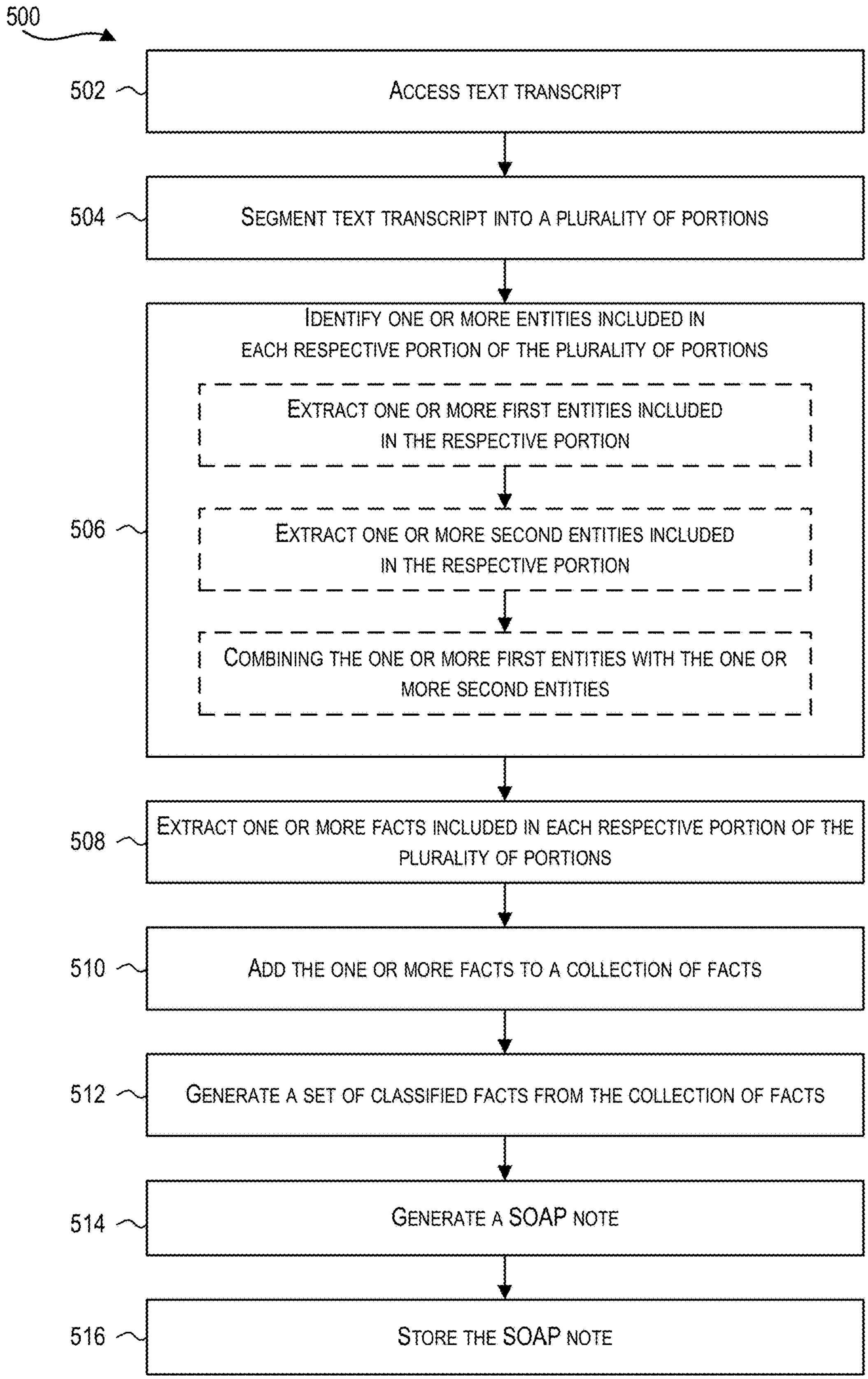
FIG. 5 depicts an example of a process for automatically generating a SOAP note using enhanced entity identification, according to some embodiments.

FIG. 5 depicts an example of a process for automatically generating a SOAP note using enhanced entity identification. The process depicted in FIG. 5 may be implemented in software (e.g., code, instructions, program) executed by one or more processing units (e.g., processors, cores) of the respective systems, hardware, or combinations thereof. The software may be stored on one or more non-transitory storage media (e.g., on a memory device). The process shown in FIG. 5 and described below is intended to be illustrative and non-limiting. Although FIG. 5 depicts the various steps occurring in a particular sequence or order, this is not intended to be limiting. In certain alternative embodiments, the steps may be performed in some different order or some steps may also be performed in parallel. In certain embodiments, such as in the embodiment depicted in FIGS. 1 and 2, the process shown FIG. 5 may be performed by environment 100 and/or the environment 200.

At block 502, a text transcript is accessed. In some implementations, the text transcript corresponds to an interaction between a first entity and a second entity. In some implementations, the first entity is a healthcare provider, and the second entity is a patient associated with the healthcare provider. In some implementations, the text transcript is stored in a cloud service provider platform such as the platform 114 described above and/or in a database such as the databases 122 described above. In some implementations, the text transcript is stored in the platform and/or the database in association with an electronic record or electronic records of the healthcare provider and/or in association with and/or within an electronic health record or electronic health records of the patient of the healthcare provider. In some implementations, the text transcript is generated by converting audio into text. The audio can be an audio recording of the interaction between the first entity and the second entity. For example, the audio recording can be an audio recording of a conversation between a healthcare provider and a patient, which can be converted into a text transcript of the conversation. To convert audio into a text transcript, one or more machine-learning models such as an ASR model can be utilized. The text transcript can be stored within the platform and/or the database, where it can be accessed.

At block 504, the text transcript is segmented into a plurality of portions. In some implementations, the text transcript includes a first number of tokens and each portion of the plurality of portions includes a second number of tokens that is less than the first number of tokens. In some implementations, segmenting the text transcript into the plurality of portions includes selecting a respective portion of the text transcript having a number of tokens corresponding to the second number of tokens and determining whether the respective portion of the text transcript satisfies predetermined criteria. In some implementations, the text transcript is segmented into equal sized chunks and/or variable sized chunks. For example, each chunk segmented can be the same size as each of the other chunks segmented. In another example, one or more chunks segmented can be a different size than other chunks segmented. In some implementations, segmenting the text transcript into the chunks includes selecting a respective portion of the text transcript that has a number of tokens corresponding to the second number of tokens and determining whether the respective portion of the text transcript satisfies predetermined criteria. In some implementations, the respective portion includes 250 tokens, which is less than the first number of tokens. In some implementations, the respective portion includes a sequence of turns of a dialog between the first entity and the second entity, where the sequence of turns includes a first turn, a last turn, and turns between the first turn and the last turn. In some implementations, determining whether the respective portion of the text transcript satisfies the predetermined criteria includes determining whether the last turn of the sequence of turns includes a question or is an incomplete sentence. In some implementations, in response to determining that the last turn of the sequence of turns includes a question, a turn in the dialog from another portion of the text transcript that answers the question is added to the respective portion such that the last turn of the sequence of turns in the modified respective portion is not a question and the modified respective portion is added to the chunks. In some implementations, in response to determining that the last turn of the sequence of turns is an incomplete sentence, a turn in the dialog from another portion of the plurality of portions is added to the respective portion such that the last turn of the sequence of turns of the modified respective portion is a complete sentence and the modified respective portion is added to the chunks.

At block 506, for each respective portion of the plurality of portions, one or more entities included in the respective portion are identified. In some implementations, identifying the one or more entities included in a respective portion includes: using a first machine-learning model to extract one or more first entities included in the respective portion; using a second machine-learning model to extract one or more second entities included in the respective portion; and combining the one or more first entities with the one or more second entities to result in the one or more entities. In some implementations, combining the one or more first entities with the one or more second entities to result in the one or more entities includes removing an entity included in the one or more second entities that are also included in the one or more first entities. In some implementations, combining the one or more first entities with the one or more second entities to result in the one or more entities includes comparing the one or more second entities to the respective portion to determine whether each second entity in the one or more second entities is included in the respective portion, and discarding any second entities in the one or more second entities that are not included in the respective portion. In some implementations, combining the one or more first entities with the one or more second entities to result in the one or more entities includes processing the one or more entities to remove additional instances of any entity that is included in the one or more entities more than once such that the one or more entities includes a single instance of each entity included in the one or more entities.

In some implementations, the one or more entities in each chunk of the chunks are identified using a machine-learning model and a machine-learning model prompt for the machine-learning model. In some implementations, the machine-learning model is an LLM. In some implementations, the LLM can be configured to identify medical or clinical or healthcare entities in the text of each respective chunk of the chunks. Examples of medical or clinical or healthcare entities include, but are not limited to, patients, doctors, medications, medication amounts, vital signs, test or examination or laboratory results, and the like. In some implementations, for each respective chunk of the chunks, a machine-learning model prompt is used to obtain results from the machine-learning model by providing the machine-learning model prompt to the machine-learning model as an input. The results can include a list (e.g., a comma separated list) or table of any entities included in the respective chunk (e.g., one entity, two entities, and so on). In some implementations, the results can be compared be to the respective chunk to determine whether any entities included in the results are not also included in the respective chunk. For example, a check can be made as whether tokens corresponding to each entity included in the results match any tokens in the respective chunk. In the case that an entity included in the results is not also included in the respective chunk, the entity can be removed from the results to result in filtered results. In some implementations, the machine-learning model prompt can include a query and context information. The query can be a query for extracting entities from the respective chunk (e.g., the query can be "Please extract all medically relevant entities of no more than 3 words from the conversation below and present them in a bullet list format."). The context information can include the respective chunk (e.g., the context information can include the text of the respective chunk). In some implementations, the machine-learning model prompt used can be automatically engineered by one or more LLMs such as the LLMs 124 and/or accessed from the platform, the databases, or another source such as the Internet.

In some implementations, the results or filtered results can be combined with results obtained from another machine-learning model and/or service that is configured to extract entities from text. In some implementations, a NER service can be accessed and used to identify one or more entities in each chunk of the chunks. In some implementations, the NER service can include a machine-learning model (e.g., a NER model) that is configured to identify medical or clinical or healthcare entities in the text of each respective chunk of the chunks. In some implementations, for each respective chunk of the chunks, the respective chunk can be provided to the NER service to obtain results from the NER service. The results can include a list (e.g., a comma separated list) of any entities included in the respective chunk. In some implementations, the results obtained from the NER service can be combined with the results or filtered results obtained from the machine-learning model to result in merged results. The merged results can include a list (e.g., a comma separated list) or table of entities included in the respective chunk. In some implementations, the merged results can be processed to determine whether any entities and/or variations of any entities included in the merged results are duplicated and remove an instance(s) of the duplicated entity from the merged results such that the processed merged results include a single instance of the duplicated entity. For example, a check can be made as to whether tokens corresponding to each entity instance included in the merged results matches tokens corresponding to the other entity instances in the merged results. In the case that an entity included in the merged results is duplicated in the merged results, additional instances of the duplicated entity can be discarded such that the processed merged results include a single instance of the duplicated entity.

At block 508, for each respective portion of the plurality of portions, one or more facts are extracted from the respective portion. In some implementations, one or more facts are extracted from each chunk of the chunks using a machine-learning model and a machine-learning model prompt for the machine-learning model. In some implementations, the machine-learning model is an LLM. In some implementations, the machine-learning model is the same as or different than the machine-learning model used to identify the one or more entities. In some implementations, for each respective chunk of the chunks, a machine-learning model prompt is used to obtain results from the machine-learning model by providing the machine-learning model prompt to the machine-learning model as an input. The results can include a list (e.g., a comma separated list) or table of any facts included in the respective chunk (e.g., one fact, two facts, and so on). In some implementations, the machine-learning model prompt can include a query and context information. The query can be a query for extracting facts from the respective chunk (e.g., the query can be "Please generate an abstractive summary of the conversation below covering the mentioned entities. The summary should be suitable for physician's notes. Each line should mention whether it is stated by the doctor or the patient. Make sure to include important numbers if they are mentioned in the conversation."). The context information can include the results, the filtered results, or the merged results and the respective chunk (e.g., the context information can include a list of entities extracted from the text of the respective chunk and the text of the respective chunk). In some implementations, the machine-learning model prompt used to extract the one or more facts can be automatically engineered by the one or more LLMs and/or accessed from the platform, the databases, or another source such as the Internet.

At block 510, the one or more facts extracted for each respective portion of the plurality of portions are added to a collection of facts. In some implementations, the one or more facts extracted for each respective portion can be combined into a collection of facts for the chunks. For example, the collection of facts for the chunks can include all the facts extracted for each of the respective chunks of the chunks.

At block 512, a set of classified facts are generated. In some implementations, the set of classified facts are generated from the collection of facts. In some implementations, the set of classified facts are generated by classifying each fact included in the collection of facts and assigning a category label to each respective fact included in the collection of facts based on a class assigned to the respective fact by the classification. The category label assigned to a respective fact included in the collection of facts can be selected from a set of category labels based on the class assigned to the respective fact. Each category label included the set of category labels can correspond to or belong to a particular SOAP note section of a SOAP to be generated. For example, as described above, a SOAP note to be generated can include a subjective section, an objective section, and an assessment and plan section, and a category label included in the set of category labels can be associated with the subjective section, a category label included in the set of category labels can be associated with the objective section, and a category label included in the set of category labels can be associated with assessment and plan section. In this way, facts included in the collection of facts can be labeled as corresponding to or belonging to or being associated with a particular note section of a SOAP note.

Each fact included in the collection of facts can be classified using a machine-learning model and a machine-learning model prompt for the machine-learning model. In some implementations, the machine-learning model is an LLM. In some implementations, the machine-learning model is the same as or different than the machine-learning model or models used to identify the one or more entities and/or extract the one or more facts. In some implementations, a machine-learning model prompt is used to obtain results from the machine-learning model by providing the machine-learning model prompt to the machine-learning model as an input. The results can include the collection of facts and category labels assigned to the facts included in collection of facts. In some implementations, each fact in the collection of facts can be assigned one or more category labels included in the set of category labels (e.g., one fact included in the collection of facts can be assigned a category label corresponding to or belonging to or associated with the subjective section of the SOAP note and a category label corresponding to or belonging to or associated with the objective section of the SOAP note).

The machine-learning model prompt for generating the set of classified facts can include a query and context information. The query can be a query for classifying facts in the collection of facts and assigning labels to the classified facts (e.g., the query can be "Please classify each of the facts in the following list of facts as corresponding to or belong to or being associated with a SOAP note section from among the following SOAP note sections. Please also assign a category label to each of the facts based on the classification of each of the facts. Each fact can have more than one category label. Please generate subset of facts organized by category label."). The context information can include the collection of facts and a list of SOAP note sections for the SOAP note that is to be generated. In some implementations, the machine-learning model prompt used to generate the set of classified facts can be automatically engineered by the one or more LLMs and/or accessed from the platform, the databases, or another source such as the Internet.

In some implementations, prior to classifying facts in the collection of facts as corresponding to or belonging to or associated with a particular SOAP note section of the SOAP note to be generated, a set of filtered facts can be generated by classifying each fact included in the collection of facts as being a medical fact or not being a medical fact. Examples of medical facts include, but are not limited to, facts pertaining to practice of medicine and/or treatment of illness and/or injuries. Each fact included in the collection of facts can be classified as being a medical fact or not being a medical fact using a machine-learning model and a machine-learning model prompt for the machine-learning model. In some implementations, the machine-learning model is an LLM. In some implementations, the machine-learning model is the same as or different than the machine-learning model or models used in the process 500. In some implementations, a machine-learning model prompt is used to obtain results from the machine-learning model by providing the machine-learning model prompt to the machine-learning model as an input. The results can include a set of filtered facts in which each fact in the set of filtered facts is medically relevant. In some implementations, the set of filtered facts can be generated prior to generating the set of classified facts and the context information of the machine-learning model prompt used to generate the set of classified facts can include the set of filtered facts (i.e., can include a set of medically relevant facts). In this way, medically relevant facts in the collection of facts can be labeled as corresponding to or belonging to or associated with a particular note section of a SOAP note.

The machine-learning model prompt for generating the set of filtered facts can include a query and context information. The query can be a query for classifying facts in the collection of facts and assigning labels to the classified facts (e.g., the query can be "Please classify and label each of the facts in the following list of facts as being medically relevant or not being medically relevant. Please generate a set of filtered facts based on the classification and labels."). The context information can include the collection of facts and examples of medically relevant facts. In some implementations, the machine-learning prompt for generating the set of filtered facts can be included in and/or combined with the machine-learning prompt for generating the set of classified facts such that providing the machine-learning model prompt to the machine-learning model prompt causes the machine-learning model to generate results that include a set of filtered and classified facts. In some implementations, the machine-learning prompt for generating the set of filtered facts can be provided to the machine-learning model before and/or after the machine-learning prompt for generating the set of classified facts is provided to the machine-learning model such that non-medically relevant facts in the collection of facts can be discarded prior to generating the SOAP note.

Any facts included the set of classified facts that have been assigned the subjective section category label (i.e., those that are classified are corresponding to or belonging to or associated with the subjective section of the SOAP note) can be organized into and/or otherwise included in a first subset of classified facts. Any facts in the set of classified facts that have been assigned the objective section category label (i.e., those that are classified are corresponding to or belonging to or associated with the objective section of the SOAP note) can be organized into and/or otherwise included in a second subset of classified facts. Any facts in the set of classified facts that include the assessment and plan section category label (i.e., those that are classified are corresponding to or belonging to or associated with the assessment and plan section of the SOAP note) can be organized and/or included in a third subset of classified facts.

At block 516, the SOAP note is generated. In some implementations, the SOAP note is generated by combining note sections of a set of note sections. In some implementations, the SOAP note can be generated by accessing a SOAP note template (e.g., a template stored in the platform and/or the database and/or accessed from another source such as the Internet) and inserting the respective SOAP note sections into respective template sections of the SOAP note template. For example, a subjective section of the SOAP note can be inserted into a corresponding section in the SOAP note template, an objective section of the SOAP note would be inserted into a corresponding section in the SOAP note template, and an assessment and plan section of the SOAP note would be inserted into a corresponding section in the SOAP note template. In some implementation, the SOAP note can be generated by generating a data structure and storing the respective SOAP note sections in the data structure.

In some implementations, the set of note sections is generated based at least in-part on the set of classified facts. In some implementations, each note section of the set of note sections corresponds to a section of the SOAP note. For example, a note section of the set of note sections can correspond to a subjective section (e.g., HPI component) of a SOAP note, a note section of the set of note sections can correspond to an objective section (e.g., ROS component) of the SOAP note, and a note section of the set of note sections can correspond to an assessment and plan section of the SOAP note. In some implementations, each note section of the set of note sections can be generated using a machine-learning model and a machine-learning model prompt for the machine-learning model. In some implementations, the machine-learning model is an LLM. In some implementations, the machine-learning model is the same as or different than the machine-learning model or models used in the process 500 and/or used to generate other note sections of the set of note sections. In some implementations, a machine-learning model prompt is used to obtain results from the machine-learning model by providing the machine-learning model prompt to the machine-learning model as an input. The results can include the respective SOAP note section. The respective SOAP note included in the results can be styled in a style and formatted in a format that corresponds to and/or matches the style and format of the SOAP note. The machine-learning model prompt for generating the respective SOAP note section can include a query and context information. The query can be a query for generating the respective SOAP note section and generating the respective SOAP note section in the style and format of the SOAP note. For example, the query to generate an HPI component of a SOAP note can be: "Given the following list of facts derived from a doctor-patient conversation, write a History of Present Illness section of a SOAP note. Do not mention any information that doesn't appear in the list of facts. Please use a paragraph format and a continuous narrative.". In another example, the query to generate an ROS component of a SOAP note can be: "You are a scribe. Do the facts contain medical symptoms? If yes, please extract all the patient's medical symptoms related information that are suitable for the Review of Systems section of a SOAP note from the facts mentioned below. Follow the instructions below while extracting the symptoms: 1. Only extract the symptoms verbalized by the patient. 2. Do not add fluff in the extracted symptoms. 3. Please do not include psychological symptoms. 4. Provide output as none if no symptom exists in the notes. 5. Only extract the medical symptoms that are present in the notes. 6. Provide the output in a bulleted list format. 7. Focus on capturing negative symptoms too meaning the symptoms that have been negated but were still discussed in the facts. 8. Do not capture diagnosis or disease." In a further example, the query to generate an Assessment and Plan component of a SOAP note can be: (i) "Generate the Assessment section of a SOAP note for the following list of facts derived from a doctor-patient conversation. The section should only include the doctor's diagnosis of the patient's problems. Do not include doctor suggestions about how to address the problems."; and (ii) "Generate the Plan section of a SOAP note for the following list of facts derived from the doctor-patient conversation." The context information can include the facts included in the first subset of classified facts, the second subset of classified facts, and/or the third subset of classified facts. For example, for the subjective section, the context information can include the facts included in the set of classified facts that have been assigned the subjective section category label (i.e., those that are classified as corresponding to or belonging to or associated with the subjective section of the SOAP note). In another example, for the objective section, the context information can include the facts included in the set of classified facts that have been assigned the objective section category label (i.e., those that are classified are corresponding to or belonging to or associated with the objective section of the SOAP note). In a further example, for the assessment and plan section, the context information can include the facts included in the set of classified facts that have been assigned the assessment and plan section category label (i.e., those that are classified are corresponding to or belonging to or associated with the assessment and plan section of the SOAP note). The context information can also include entity information such as medical or healthcare information for the patient of the interaction (e.g., patient's age, gender, weight, and so on). The medical or health information can be derived from an electronic health record for the patient such as those described above and stored in the platform and/or database. In some implementations, the machine-learning model prompt used to generate respective note sections of the set of note section can be automatically engineered by the one or more LLMs, and/or accessed from the platform, the databases, or another source such as the Internet.

At block 516, the SOAP note is stored. In some implementations, the SOAP note is stored in a database associated with at least one of the first entity and the second entity. In some implementations, storing the SOAP note in the database includes storing the SOAP note in an electronic health record associated with the patient. In some implementations, the SOAP note and/or the data structure that includes the SOAP note can be stored in the platform and/or the databases and/or the SOAP note and/or the data structure that includes the SOAP note can be sent to a remote location such as one or more client devices such as the client devices 110. In some implementations, the SOAP note and/or the data structure that includes the SOAP note is stored in a database that is associated with at least one of the first entity and the second entity. In this way, an automatically generated SOAP note that documents an encounter between a healthcare provider and a patient can be stored in the patient's electronic health record such that one or more other entities such as one or more other healthcare providers can access the SOAP note at a later time.

Examples of Cloud Infrastructure Architectures

The term cloud service is generally used to refer to a service that is made available by a cloud service provider (CSP) to users (e.g., cloud service customers) on demand (e.g., via a subscription model) using systems and infrastructure (cloud infrastructure) provided by the CSP. Typically, the servers and systems that make up the CSP's infrastructure are separate from the user's own on-premise servers and systems. Users can thus avail themselves of cloud services provided by the CSP without having to purchase separate hardware and software resources for the services. Cloud services are designed to provide a subscribing user easy, scalable access to applications and computing resources without the user having to invest in procuring the infrastructure that is used for providing the services.

There are several cloud service providers that offer various types of cloud services. As discussed herein, there are various types or models of cloud services including IaaS, software as a service (SaaS), platform as a service (PaaS), and others. A user can subscribe to one or more cloud services provided by a CSP. The user can be any entity such as an individual, an organization, an enterprise, and the like. When a user subscribes to or registers for a service provided by a CSP, a tenancy or an account is created for that user. The user can then, via this account, access the subscribed-to one or more cloud resources associated with the account.

As noted above, IaaS is one particular type of cloud computing. IaaS can be configured to provide virtualized computing resources over a public network (e.g., the Internet). In an IaaS model, a cloud computing provider can host the infrastructure components (e.g., servers, storage devices, network nodes (e.g., hardware), deployment software, platform virtualization (e.g., a hypervisor layer), or the like). In some cases, an IaaS provider may also supply a variety of services to accompany those infrastructure components (example services include billing software, monitoring software, logging software, load balancing software, clustering software, etc.). Thus, as these services may be policy-driven, IaaS users may be able to implement policies to drive load balancing to maintain application availability and performance.

In some instances, IaaS customers may access resources and services through a wide area network (WAN), such as the Internet, and can use the cloud provider's services to install the remaining elements of an application stack. For example, the user can log in to the IaaS platform to create virtual machines (VMs), install operating systems (OSs) on each VM, deploy middleware such as databases, create storage buckets for workloads and backups, and even install enterprise software into that VM. Customers can then use the provider's services to perform various functions, including balancing network traffic, troubleshooting application issues, monitoring performance, managing disaster recovery, etc.

In most cases, a cloud computing model will require the participation of a cloud provider. The cloud provider may, but need not be, a third-party service that specializes in providing (e.g., offering, renting, selling) IaaS. An entity might also opt to deploy a private cloud, becoming its own provider of infrastructure services.

In some examples, IaaS deployment is the process of putting a new application, or a new version of an application, onto a prepared application server or the like. It may also include the process of preparing the server (e.g., installing libraries, daemons, etc.). This is often managed by the cloud provider, below the hypervisor layer (e.g., the servers, storage, network hardware, and virtualization). Thus, the customer may be responsible for handling (OS), middleware, and/or application deployment (e.g., on self-service virtual machines (e.g., that can be spun up on demand) or the like.

In some examples, IaaS provisioning may refer to acquiring computers or virtual hosts for use, and even installing needed libraries or services on them. In most cases, deployment does not include provisioning, and the provisioning may need to be performed first.

In some cases, there are two different challenges for IaaS provisioning. First, there is the initial challenge of provisioning the initial set of infrastructure before anything is running. Second, there is the challenge of evolving the existing infrastructure (e.g., adding new services, changing services, removing services, etc.) once everything has been provisioned. In some cases, these two challenges may be addressed by enabling the configuration of the infrastructure to be defined declaratively. In other words, the infrastructure (e.g., what components are needed and how they interact) can be defined by one or more configuration files. Thus, the overall topology of the infrastructure (e.g., what resources depend on which, and how they each work together) can be described declaratively. In some instances, once the topology is defined, a workflow can be generated that creates and/or manages the different components described in the configuration files.

In some examples, an infrastructure may have many interconnected elements. For example, there may be one or more virtual private clouds (VPCs) (e.g., a potentially on-demand pool of configurable and/or shared computing resources), also known as a core network. In some examples, there may also be one or more inbound/outbound traffic group rules provisioned to define how the inbound and/or outbound traffic of the network will be set up and one or more virtual machines (VMs). Other infrastructure elements may also be provisioned, such as a load balancer, a database, or the like. As more and more infrastructure elements are desired and/or added, the infrastructure may incrementally evolve.

In some instances, continuous deployment techniques may be employed to enable deployment of infrastructure code across various virtual computing environments. Additionally, the described techniques can enable infrastructure management within these environments. In some examples, service teams can write code that is desired to be deployed to one or more, but often many, different production environments (e.g., across various different geographic locations, sometimes spanning the entire world). However, in some examples, the infrastructure on which the code will be deployed must first be set up. In some instances, the provisioning can be done manually, a provisioning tool may be utilized to provision the resources, and/or deployment tools may be utilized to deploy the code once the infrastructure is provisioned.

Figure 6:
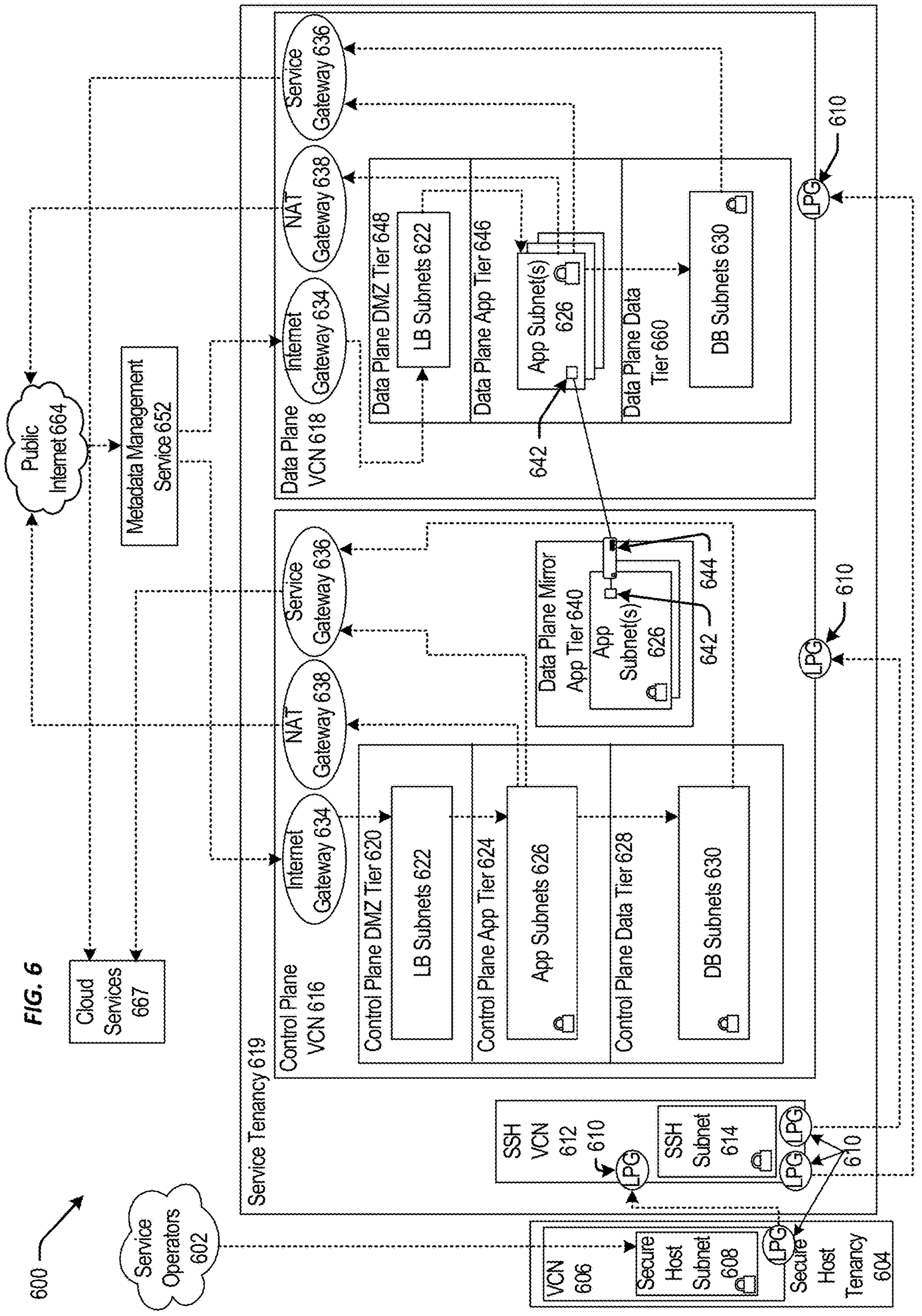
FIG. 6 is a block diagram illustrating one pattern for implementing a cloud infrastructure as a service system according to certain embodiments.

FIG. 6 is a block diagram 600 illustrating an example pattern of an IaaS architecture, according to at least one embodiment. Service operators 602 can be communicatively coupled to a secure host tenancy 604 that can include a virtual cloud network (VCN) 606 and a secure host subnet 608. In some examples, the service operators 602 may be using one or more client computing devices, which may be portable handheld devices (e.g., an iPhone®, cellular telephone, an iPad®, computing tablet, a personal digital assistant (PDA)) or wearable devices (e.g., a Google Glass® head mounted display), running software such as Microsoft Windows Mobile®, and/or a variety of mobile operating systems such as iOS, Windows Phone, Android, BlackBerry 6, Palm OS, and the like, and being Internet, e-mail, short message service (SMS), Blackberry®, or other communication protocol enabled. Alternatively, the client computing devices can be general purpose personal computers including, by way of example, personal computers and/or laptop computers running various versions of Microsoft Windows®, Apple Macintosh®, and/or Linux operating systems. The client computing devices can be workstation computers running any of a variety of commercially-available UNIX® or UNIX-like operating systems, including without limitation the variety of GNU/Linux operating systems, such as for example, Google Chrome OS. Alternatively, or in addition, client computing devices may be any other electronic device, such as a thin-client computer, an Internet-enabled gaming system (e.g., a Microsoft Xbox gaming console with or without a Kinect® gesture input device), and/or a personal messaging device, capable of communicating over a network that can access the VCN 606 and/or the Internet.

The VCN 606 can include a local peering gateway (LPG) 610 that can be communicatively coupled to a secure shell (SSH) VCN 612 via an LPG 610 contained in the SSH VCN 612. The SSH VCN 612 can include an SSH subnet 614, and the SSH VCN 612 can be communicatively coupled to a control plane VCN 616 via the LPG 610 contained in the control plane VCN 616. Also, the SSH VCN 612 can be communicatively coupled to a data plane VCN 618 via an LPG 610. The control plane VCN 616 and the data plane VCN 618 can be contained in a service tenancy 619 that can be owned and/or operated by the IaaS provider.

The control plane VCN 616 can include a control plane demilitarized zone (DMZ) tier 620 that acts as a perimeter network (e.g., portions of a corporate network between the corporate intranet and external networks). The DMZ-based servers may have restricted responsibilities and help keep breaches contained. Additionally, the control plane DMZ tier 620 can include one or more load balancer (LB) subnet(s) 622, a control plane app tier 624 that can include app subnet(s) 626, a control plane data tier 628 that can include database (DB) subnet(s) 630 (e.g., frontend DB subnet(s) and/or backend DB subnet(s)). The LB subnet(s) 622 contained in the control plane DMZ tier 620 can be communicatively coupled to the app subnet(s) 626 contained in the control plane app tier 624 and an Internet gateway 634 that can be contained in the control plane VCN 616, and the app subnet(s) 626 can be communicatively coupled to the DB subnet(s) 630 contained in the control plane data tier 628 and a service gateway 636 and a network address translation (NAT) gateway 638. The control plane VCN 616 can include the service gateway 636 and the NAT gateway 638.

The control plane VCN 616 can include a data plane mirror app tier 640 that can include app subnet(s) 626. The app subnet(s) 626 contained in the data plane mirror app tier 640 can include a virtual network interface controller (VNIC) 642 that can execute a compute instance 644. The compute instance 644 can communicatively couple the app subnet(s) 626 of the data plane mirror app tier 640 to app subnet(s) 626 that can be contained in a data plane app tier 646.

The data plane VCN 618 can include the data plane app tier 646, a data plane DMZ tier 648, and a data plane data tier 660. The data plane DMZ tier 648 can include LB subnet(s) 622 that can be communicatively coupled to the app subnet(s) 626 of the data plane app tier 646 and the Internet gateway 634 of the data plane VCN 618. The app subnet(s) 626 can be communicatively coupled to the service gateway 636 of the data plane VCN 618 and the NAT gateway 638 of the data plane VCN 618. The data plane data tier 660 can also include the DB subnet(s) 630 that can be communicatively coupled to the app subnet(s) 626 of the data plane app tier 646.

The Internet gateway 634 of the control plane VCN 616 and of the data plane VCN 618 can be communicatively coupled to a metadata management service 662 that can be communicatively coupled to public Internet 664. Public Internet 664 can be communicatively coupled to the NAT gateway 638 of the control plane VCN 616 and of the data plane VCN 618. The service gateway 636 of the control plane VCN 616 and of the data plane VCN 618 can be communicatively coupled to cloud services 667.

In some examples, the service gateway 636 of the control plane VCN 616 or of the data plane VCN 618 can make application programming interface (API) calls to cloud services 667 without going through public Internet 664. The API calls to cloud services 667 from the service gateway 636 can be one-way: the service gateway 636 can make API calls to cloud services 667, and cloud services 667 can send requested data to the service gateway 636. But, cloud services 667 may not initiate API calls to the service gateway 636.

In some examples, the secure host tenancy 604 can be directly connected to the service tenancy 619, which may be otherwise isolated. The secure host subnet 608 can communicate with the SSH subnet 614 through an LPG 610 that may enable two-way communication over an otherwise isolated system. Connecting the secure host subnet 608 to the SSH subnet 614 may give the secure host subnet 608 access to other entities within the service tenancy 619.

The control plane VCN 616 may allow users of the service tenancy 619 to set up or otherwise provision desired resources. Desired resources provisioned in the control plane VCN 616 may be deployed or otherwise used in the data plane VCN 618. In some examples, the control plane VCN 616 can be isolated from the data plane VCN 618, and the data plane mirror app tier 640 of the control plane VCN 616 can communicate with the data plane app tier 646 of the data plane VCN 618 via VNICs 642 that can be contained in the data plane mirror app tier 640 and the data plane app tier 646.

In some examples, users of the system, or customers, can make requests, for example create, read, update, or delete (CRUD) operations, through public Internet 664 that can communicate the requests to the metadata management service 662. The metadata management service 662 can communicate the request to the control plane VCN 616 through the Internet gateway 634. The request can be received by the LB subnet(s) 622 contained in the control plane DMZ tier 620. The LB subnet(s) 622 may determine that the request is valid, and in response to this determination, the LB subnet(s) 622 can transmit the request to app subnet(s) 626 contained in the control plane app tier 624. If the request is validated and requires a call to public Internet 664, the call to public Internet 664 may be transmitted to the NAT gateway 638 that can make the call to public Internet 664. Metadata that may be desired to be stored by the request can be stored in the DB subnet(s) 630.

In some examples, the data plane mirror app tier 640 can facilitate direct communication between the control plane VCN 616 and the data plane VCN 618. For example, changes, updates, or other suitable modifications to configuration may be desired to be applied to the resources contained in the data plane VCN 618. Via a VNIC 642, the control plane VCN 616 can directly communicate with, and can thereby execute the changes, updates, or other suitable modifications to configuration to, resources contained in the data plane VCN 618.

In some embodiments, the control plane VCN 616 and the data plane VCN 618 can be contained in the service tenancy 619. In this case, the user, or the customer, of the system may not own or operate either the control plane VCN 616 or the data plane VCN 618. Instead, the IaaS provider may own or operate the control plane VCN 616 and the data plane VCN 618, both of which may be contained in the service tenancy 619. This embodiment can enable isolation of networks that may prevent users or customers from interacting with other users', or other customers', resources. Also, this embodiment may allow users or customers of the system to store databases privately without needing to rely on public Internet 664, which may not have a desired level of threat prevention, for storage.

In other embodiments, the LB subnet(s) 622 contained in the control plane VCN 616 can be configured to receive a signal from the service gateway 636. In this embodiment, the control plane VCN 616 and the data plane VCN 618 may be configured to be called by a customer of the IaaS provider without calling public Internet 664. Customers of the IaaS provider may desire this embodiment since database(s) that the customers use may be controlled by the IaaS provider and may be stored on the service tenancy 619, which may be isolated from public Internet 664.

Figure 7:
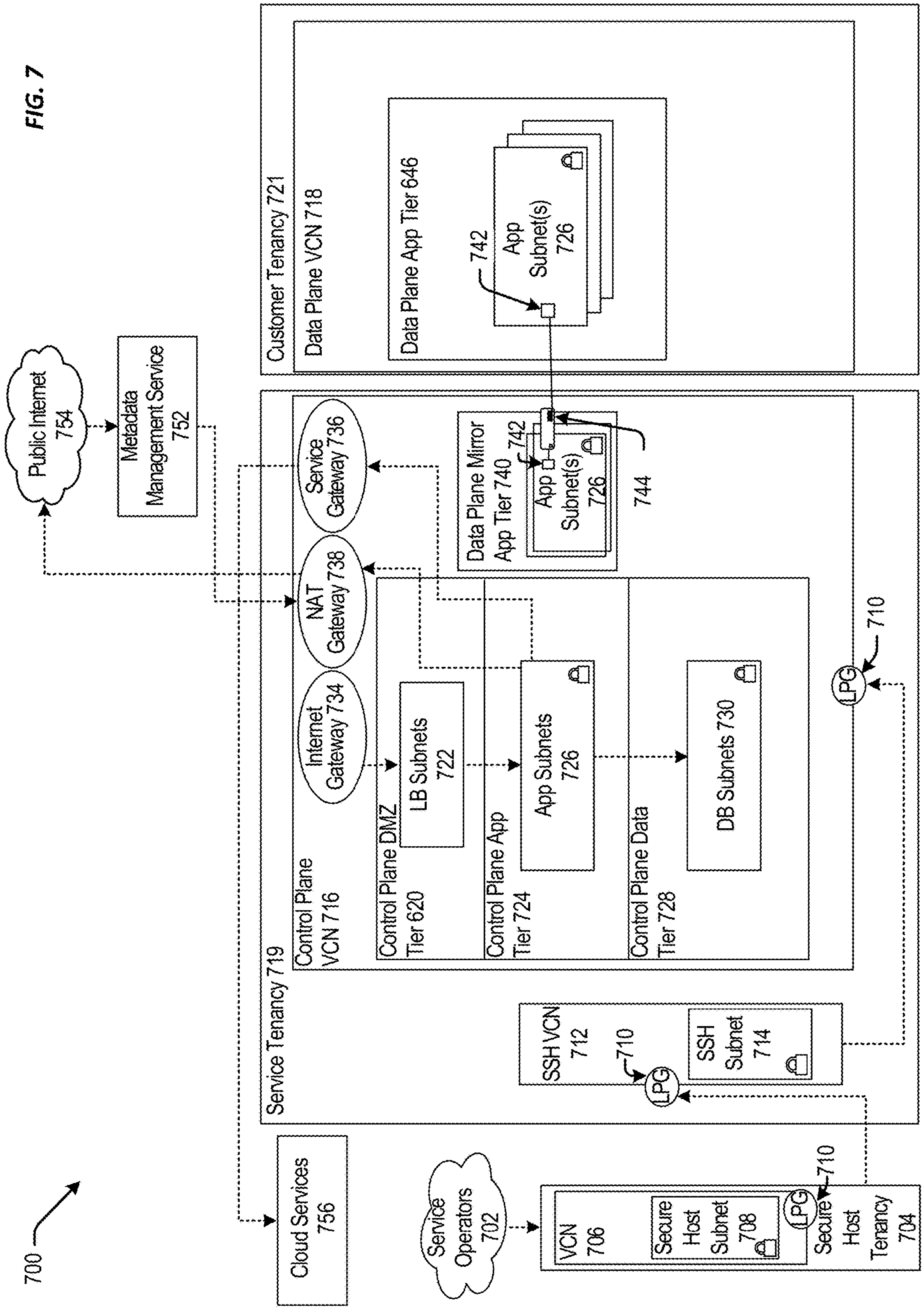
FIG. 7 is a block diagram illustrating another pattern for implementing a cloud infrastructure as a service system according to certain embodiments.

FIG. 7 is a block diagram 700 illustrating another example pattern of an IaaS architecture, according to at least one embodiment. Service operators 702 (e.g., service operators 602 of FIG. 6) can be communicatively coupled to a secure host tenancy 704 (e.g., the secure host tenancy 604 of FIG. 6) that can include a virtual cloud network (VCN) 706 (e.g., the VCN 606 of FIG. 6) and a secure host subnet 708 (e.g., the secure host subnet 608 of FIG. 6). The VCN 606 can include a local peering gateway (LPG) 710 (e.g., the LPG 610 of FIG. 6) that can be communicatively coupled to a secure shell (SSH) VCN 712 (e.g., the SSH VCN 612 of FIG. 6) via an LPG 710 contained in the SSH VCN 712. The SSH VCN 712 can include an SSH subnet 714 (e.g., the SSH subnet 614 of FIG. 6), and the SSH VCN 712 can be communicatively coupled to a control plane VCN 716 (e.g., the control plane VCN 616 of FIG. 6) via an LPG 710 contained in the control plane VCN 716. The control plane VCN 716 can be contained in a service tenancy 719 (e.g., the service tenancy 619 of FIG. 6), and the data plane VCN 718 (e.g., the data plane VCN 618 of FIG. 6) can be contained in a customer tenancy 721 that may be owned or operated by users, or customers, of the system.

The control plane VCN 716 can include a control plane DMZ tier 720 (e.g., the control plane DMZ tier 620 of FIG. 6) that can include LB subnet(s) 722 (e.g., LB subnet(s) 622 of FIG. 6), a control plane app tier 724 (e.g., the control plane app tier 624 of FIG. 6) that can include app subnet(s) 726 (e.g., app subnet(s) 626 of FIG. 6), a control plane data tier 728 (e.g., the control plane data tier 628 of FIG. 6) that can include database (DB) subnet(s) 730 (e.g., similar to DB subnet(s) 630 of FIG. 6). The LB subnet(s) 722 contained in the control plane DMZ tier 720 can be communicatively coupled to the app subnet(s) 726 contained in the control plane app tier 724 and an Internet gateway 734 (e.g., the Internet gateway 634 of FIG. 6) that can be contained in the control plane VCN 716, and the app subnet(s) 726 can be communicatively coupled to the DB subnet(s) 730 contained in the control plane data tier 728 and a service gateway 736 (e.g., the service gateway 636 of FIG. 6) and a network address translation (NAT) gateway 738 (e.g., the NAT gateway 638 of FIG. 6). The control plane VCN 716 can include the service gateway 736 and the NAT gateway 738.

The control plane VCN 716 can include a data plane mirror app tier 740 (e.g., the data plane mirror app tier 640 of FIG. 6) that can include app subnet(s) 726. The app subnet(s) 726 contained in the data plane mirror app tier 740 can include a virtual network interface controller (VNIC) 742 (e.g., the VNIC of 642) that can execute a compute instance 744 (e.g., similar to the compute instance 644 of FIG. 6). The compute instance 744 can facilitate communication between the app subnet(s) 726 of the data plane mirror app tier 740 and the app subnet(s) 726 that can be contained in a data plane app tier 746 (e.g., the data plane app tier 646 of FIG. 6) via the VNIC 742 contained in the data plane mirror app tier 740 and the VNIC 742 contained in the data plane app tier 746.

The Internet gateway 734 contained in the control plane VCN 716 can be communicatively coupled to a metadata management service 752 (e.g., the metadata management service 662 of FIG. 6) that can be communicatively coupled to public Internet 754 (e.g., public Internet 664 of FIG. 6). Public Internet 754 can be communicatively coupled to the NAT gateway 738 contained in the control plane VCN 716. The service gateway 736 contained in the control plane VCN 716 can be communicatively coupled to cloud services 756 (e.g., cloud services 667 of FIG. 6).

In some examples, the data plane VCN 718 can be contained in the customer tenancy 721. In this case, the IaaS provider may provide the control plane VCN 716 for each customer, and the IaaS provider may, for each customer, set up a unique compute instance 744 that is contained in the service tenancy 719. Each compute instance 744 may allow communication between the control plane VCN 716, contained in the service tenancy 719, and the data plane VCN 718 that is contained in the customer tenancy 721. The compute instance 744 may allow resources, that are provisioned in the control plane VCN 716 that is contained in the service tenancy 719, to be deployed or otherwise used in the data plane VCN 718 that is contained in the customer tenancy 721.

In other examples, the customer of the IaaS provider may have databases that live in the customer tenancy 721. In this example, the control plane VCN 716 can include the data plane mirror app tier 740 that can include app subnet(s) 726. The data plane mirror app tier 740 can reside in the data plane VCN 718, but the data plane mirror app tier 740 may not live in the data plane VCN 718. That is, the data plane mirror app tier 740 may have access to the customer tenancy 721, but the data plane mirror app tier 740 may not exist in the data plane VCN 718 or be owned or operated by the customer of the IaaS provider. The data plane mirror app tier 740 may be configured to make calls to the data plane VCN 718 but may not be configured to make calls to any entity contained in the control plane VCN 716. The customer may desire to deploy or otherwise use resources in the data plane VCN 718 that are provisioned in the control plane VCN 716, and the data plane mirror app tier 740 can facilitate the desired deployment, or other usage of resources, of the customer.

In some embodiments, the customer of the IaaS provider can apply filters to the data plane VCN 718. In this embodiment, the customer can determine what the data plane VCN 718 can access, and the customer may restrict access to public Internet 754 from the data plane VCN 718. The IaaS provider may not be able to apply filters or otherwise control access of the data plane VCN 718 to any outside networks or databases. Applying filters and controls by the customer onto the data plane VCN 718, contained in the customer tenancy 721, can help isolate the data plane VCN 718 from other customers and from public Internet 754.

In some embodiments, cloud services 756 can be called by the service gateway 736 to access services that may not exist on public Internet 754, on the control plane VCN 716, or on the data plane VCN 718. The connection between cloud services 756 and the control plane VCN 716 or the data plane VCN 718 may not be live or continuous. Cloud services 756 may exist on a different network owned or operated by the IaaS provider. Cloud services 756 may be configured to receive calls from the service gateway 736 and may be configured to not receive calls from public Internet 754. Some cloud services 756 may be isolated from other cloud services 756, and the control plane VCN 716 may be isolated from cloud services 756 that may not be in the same region as the control plane VCN 716. For example, the control plane VCN 716 may be located in "Region 1," and cloud service "Deployment 8," may be located in Region 1 and in "Region 2." If a call to Deployment 8 is made by the service gateway 736 contained in the control plane VCN 716 located in Region 1, the call may be transmitted to Deployment 8 in Region 1. In this example, the control plane VCN 716, or Deployment 8 in Region 1, may not be communicatively coupled to, or otherwise in communication with, Deployment 8 in Region 2.

Figure 8:
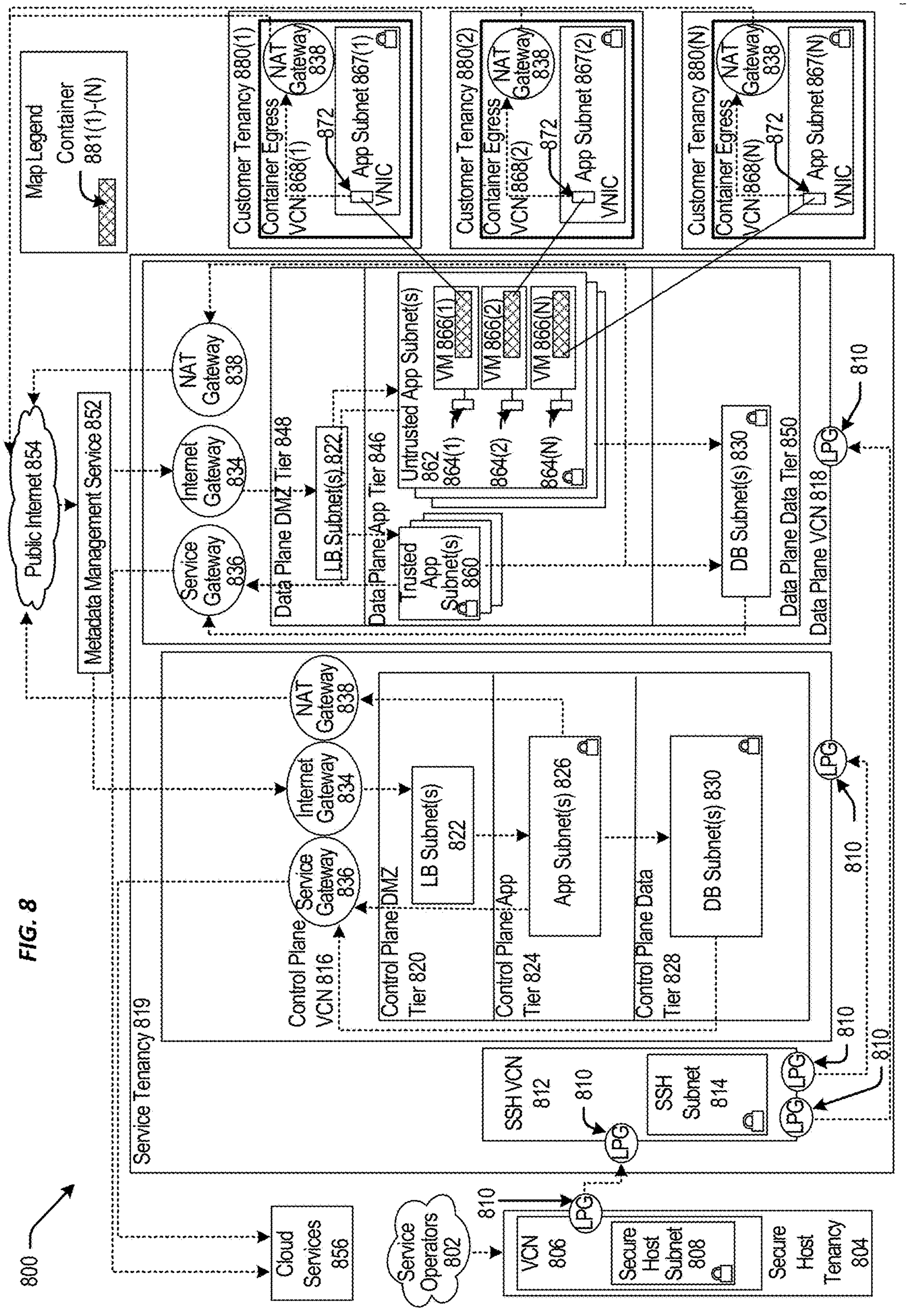
FIG. 8 is a block diagram illustrating another pattern for implementing a cloud infrastructure as a service system according to certain embodiments.

FIG. 8 is a block diagram 800 illustrating another example pattern of an IaaS architecture, according to at least one embodiment. Service operators 802 (e.g., service operators 602 of FIG. 6) can be communicatively coupled to a secure host tenancy 804 (e.g., the secure host tenancy 604 of FIG. 6) that can include a virtual cloud network (VCN) 806 (e.g., the VCN 606 of FIG. 6) and a secure host subnet 808 (e.g., the secure host subnet 608 of FIG. 6). The VCN 806 can include an LPG 810 (e.g., the LPG 610 of FIG. 6) that can be communicatively coupled to an SSH VCN 812 (e.g., the SSH VCN 612 of FIG. 6) via an LPG 810 contained in the SSH VCN 812. The SSH VCN 812 can include an SSH subnet 814 (e.g., the SSH subnet 614 of FIG. 6), and the SSH VCN 812 can be communicatively coupled to a control plane VCN 816 (e.g., the control plane VCN 616 of FIG. 6) via an LPG 810 contained in the control plane VCN 816 and to a data plane VCN 818 (e.g., the data plane VCN 618 of FIG. 6) via an LPG 810 contained in the data plane VCN 818. The control plane VCN 816 and the data plane VCN 818 can be contained in a service tenancy 819 (e.g., the service tenancy 619 of FIG. 6).

The control plane VCN 816 can include a control plane DMZ tier 820 (e.g., the control plane DMZ tier 620 of FIG. 6) that can include load balancer (LB) subnet(s) 822 (e.g., LB subnet(s) 622 of FIG. 6), a control plane app tier 824 (e.g., the control plane app tier 624 of FIG. 6) that can include app subnet(s) 826 (e.g., similar to app subnet(s) 626 of FIG. 6), a control plane data tier 828 (e.g., the control plane data tier 628 of FIG. 6) that can include DB subnet(s) 830. The LB subnet(s) 822 contained in the control plane DMZ tier 820 can be communicatively coupled to the app subnet(s) 826 contained in the control plane app tier 824 and to an Internet gateway 834 (e.g., the Internet gateway 634 of FIG. 6) that can be contained in the control plane VCN 816, and the app subnet(s) 826 can be communicatively coupled to the DB subnet(s) 830 contained in the control plane data tier 828 and to a service gateway 836 (e.g., the service gateway of FIG. 6) and a network address translation (NAT) gateway 838 (e.g., the NAT gateway 638 of FIG. 6). The control plane VCN 816 can include the service gateway 836 and the NAT gateway 838.

The data plane VCN 818 can include a data plane app tier 846 (e.g., the data plane app tier 646 of FIG. 6), a data plane DMZ tier 848 (e.g., the data plane DMZ tier 648 of FIG. 6), and a data plane data tier 850 (e.g., the data plane data tier 660 of FIG. 6). The data plane DMZ tier 848 can include LB subnet(s) 822 that can be communicatively coupled to trusted app subnet(s) 860 and untrusted app subnet(s) 862 of the data plane app tier 846 and the Internet gateway 834 contained in the data plane VCN 818. The trusted app subnet(s) 860 can be communicatively coupled to the service gateway 836 contained in the data plane VCN 818, the NAT gateway 838 contained in the data plane VCN 818, and DB subnet(s) 830 contained in the data plane data tier 850. The untrusted app subnet(s) 862 can be communicatively coupled to the service gateway 836 contained in the data plane VCN 818 and DB subnet(s) 830 contained in the data plane data tier 850. The data plane data tier 850 can include DB subnet(s) 830 that can be communicatively coupled to the service gateway 836 contained in the data plane VCN 818.

The untrusted app subnet(s) 862 can include one or more primary VNICs 864(1)-(N) that can be communicatively coupled to tenant virtual machines (VMs) 866(1)-(N). Each tenant VM 866(1)-(N) can be communicatively coupled to a respective app subnet 867(1)-(N) that can be contained in respective container egress VCNs 868(1)-(N) that can be contained in respective customer tenancies 880(1)-(N). Respective secondary VNICs 882(1)-(N) can facilitate communication between the untrusted app subnet(s) 862 contained in the data plane VCN 818 and the app subnet contained in the container egress VCNs 868(1)-(N). Each container egress VCNs 868(1)-(N) can include a NAT gateway 838 that can be communicatively coupled to public Internet 854 (e.g., public Internet 664 of FIG. 6).

The Internet gateway 834 contained in the control plane VCN 816 and contained in the data plane VCN 818 can be communicatively coupled to a metadata management service 852 (e.g., the metadata management service 662 of FIG. 6) that can be communicatively coupled to public Internet 854. Public Internet 854 can be communicatively coupled to the NAT gateway 838 contained in the control plane VCN 816 and contained in the data plane VCN 818. The service gateway 836 contained in the control plane VCN 816 and contained in the data plane VCN 818 can be communicatively coupled to cloud services 856.

In some embodiments, the data plane VCN 818 can be integrated with customer tenancies 880. This integration can be useful or desirable for customers of the IaaS provider in some cases such as a case that may desire support when executing code. The customer may provide code to run that may be destructive, may communicate with other customer resources, or may otherwise cause undesirable effects. In response to this, the IaaS provider may determine whether to run code given to the IaaS provider by the customer.

In some examples, the customer of the IaaS provider may grant temporary network access to the IaaS provider and request a function to be attached to the data plane app tier 846. Code to run the function may be executed in the VMs 866(1)-(N), and the code may not be configured to run anywhere else on the data plane VCN 818. Each VM 866(1)-(N) may be connected to one customer tenancy 880. Respective containers 881(1)-(N) contained in the VMs 866(1)-(N) may be configured to run the code. In this case, there can be a dual isolation (e.g., the containers 881(1)-(N) running code, where the containers 881(1)-(N) may be contained in at least the VM 866(1)-(N) that are contained in the untrusted app subnet(s) 862), which may help prevent incorrect or otherwise undesirable code from damaging the network of the IaaS provider or from damaging a network of a different customer. The containers 881(1)-(N) may be communicatively coupled to the customer tenancy 880 and may be configured to transmit or receive data from the customer tenancy 880. The containers 881(1)-(N) may not be configured to transmit or receive data from any other entity in the data plane VCN 818. Upon completion of running the code, the IaaS provider may kill or otherwise dispose of the containers 881(1)-(N).

In some embodiments, the trusted app subnet(s) 860 may run code that may be owned or operated by the IaaS provider. In this embodiment, the trusted app subnet(s) 860 may be communicatively coupled to the DB subnet(s) 830 and be configured to execute CRUD operations in the DB subnet(s) 830. The untrusted app subnet(s) 862 may be communicatively coupled to the DB subnet(s) 830, but in this embodiment, the untrusted app subnet(s) may be configured to execute read operations in the DB subnet(s) 830. The containers 881(1)-(N) that can be contained in the VM 866(1)-(N) of each customer and that may run code from the customer may not be communicatively coupled with the DB subnet(s) 830.

In other embodiments, the control plane VCN 816 and the data plane VCN 818 may not be directly communicatively coupled. In this embodiment, there may be no direct communication between the control plane VCN 816 and the data plane VCN 818. However, communication can occur indirectly through at least one method. An LPG 810 may be established by the IaaS provider that can facilitate communication between the control plane VCN 816 and the data plane VCN 818. In another example, the control plane VCN 816 or the data plane VCN 818 can make a call to cloud services 856 via the service gateway 836. For example, a call to cloud services 856 from the control plane VCN 816 can include a request for a service that can communicate with the data plane VCN 818.

Figure 9:
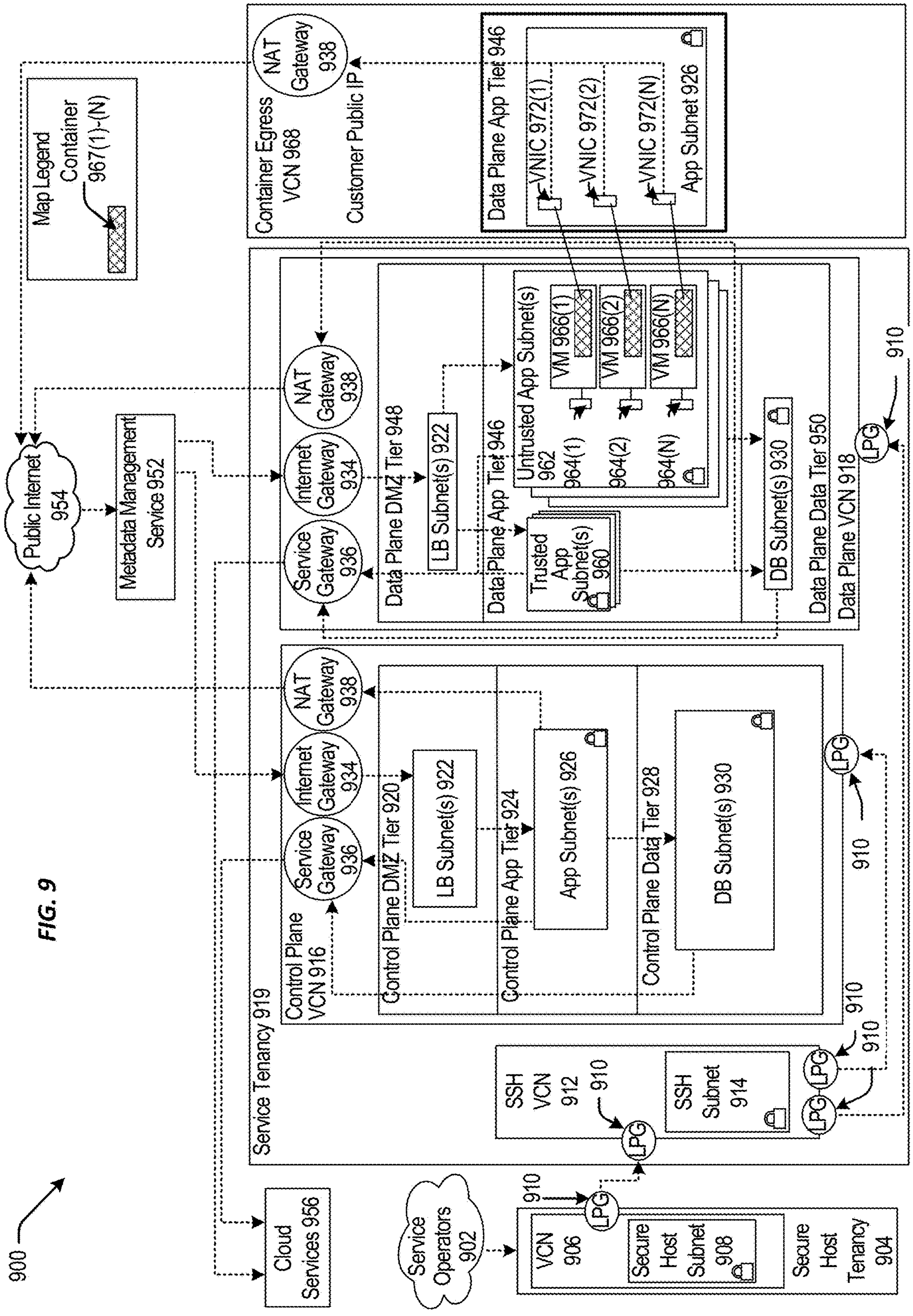
FIG. 9 is a block diagram illustrating another pattern for implementing a cloud infrastructure as a service system according to certain embodiments.

FIG. 9 is a block diagram 900 illustrating another example pattern of an IaaS architecture, according to at least one embodiment. Service operators 902 (e.g., service operators 602 of FIG. 6) can be communicatively coupled to a secure host tenancy 904 (e.g., the secure host tenancy 604 of FIG. 6) that can include a virtual cloud network (VCN) 906 (e.g., the VCN 606 of FIG. 6) and a secure host subnet 908 (e.g., the secure host subnet 608 of FIG. 6). The VCN 906 can include an LPG 910 (e.g., the LPG 610 of FIG. 6) that can be communicatively coupled to an SSH VCN 912 (e.g., the SSH VCN 612 of FIG. 6) via an LPG 910 contained in the SSH VCN 912. The SSH VCN 912 can include an SSH subnet 914 (e.g., the SSH subnet 614 of FIG. 6), and the SSH VCN 912 can be communicatively coupled to a control plane VCN 916 (e.g., the control plane VCN 616 of FIG. 6) via an LPG 910 contained in the control plane VCN 916 and to a data plane VCN 918 (e.g., the data plane VCN 618 of FIG. 6) via an LPG 910 contained in the data plane VCN 918. The control plane VCN 916 and the data plane VCN 918 can be contained in a service tenancy 919 (e.g., the service tenancy 619 of FIG. 6).

The control plane VCN 916 can include a control plane DMZ tier 920 (e.g., the control plane DMZ tier 620 of FIG. 6) that can include LB subnet(s) 922 (e.g., LB subnet(s) 622 of FIG. 6), a control plane app tier 924 (e.g., the control plane app tier 624 of FIG. 6) that can include app subnet(s) 926 (e.g., app subnet(s) 626 of FIG. 6), a control plane data tier 928 (e.g., the control plane data tier 628 of FIG. 6) that can include DB subnet(s) 930 (e.g., DB subnet(s) 730 of FIG. 7). The LB subnet(s) 922 contained in the control plane DMZ tier 920 can be communicatively coupled to the app subnet(s) 926 contained in the control plane app tier 924 and to an Internet gateway 934 (e.g., the Internet gateway 634 of FIG. 6) that can be contained in the control plane VCN 916, and the app subnet(s) 926 can be communicatively coupled to the DB subnet(s) 930 contained in the control plane data tier 928 and to a service gateway 936 (e.g., the service gateway of FIG. 6) and a network address translation (NAT) gateway 938 (e.g., the NAT gateway 638 of FIG. 6). The control plane VCN 916 can include the service gateway 936 and the NAT gateway 938.

The data plane VCN 918 can include a data plane app tier 946 (e.g., the data plane app tier 646 of FIG. 6), a data plane DMZ tier 948 (e.g., the data plane DMZ tier 648 of FIG. 6), and a data plane data tier 950 (e.g., the data plane data tier 660 of FIG. 6). The data plane DMZ tier 948 can include LB subnet(s) 922 that can be communicatively coupled to trusted app subnet(s) 960 (e.g., trusted app subnet(s) 770 of FIG. 7) and untrusted app subnet(s) 962 (e.g., untrusted app subnet(s) 772 of FIG. 7) of the data plane app tier 946 and the Internet gateway 934 contained in the data plane VCN 918. The trusted app subnet(s) 960 can be communicatively coupled to the service gateway 936 contained in the data plane VCN 918, the NAT gateway 938 contained in the data plane VCN 918, and DB subnet(s) 930 contained in the data plane data tier 950. The untrusted app subnet(s) 962 can be communicatively coupled to the service gateway 936 contained in the data plane VCN 918 and DB subnet(s) 930 contained in the data plane data tier 950. The data plane data tier 950 can include DB subnet(s) 930 that can be communicatively coupled to the service gateway 936 contained in the data plane VCN 918.

The untrusted app subnet(s) 962 can include primary VNICs 964(1)-(N) that can be communicatively coupled to tenant virtual machines (VMs) 966(1)-(N) residing within the untrusted app subnet(s) 962. Each tenant VM 966(1)-(N) can run code in a respective container 967(1)-(N), and be communicatively coupled to an app subnet 926 that can be contained in a data plane app tier 946 that can be contained in a container egress VCN 968. Respective secondary VNICs 972(1)-(N) can facilitate communication between the untrusted app subnet(s) 962 contained in the data plane VCN 918 and the app subnet contained in the container egress VCN 968. The container egress VCN can include a NAT gateway 938 that can be communicatively coupled to public Internet 954 (e.g., public Internet 664 of FIG. 6).

The Internet gateway 934 contained in the control plane VCN 916 and contained in the data plane VCN 918 can be communicatively coupled to a metadata management service 952 (e.g., the metadata management service 662 of FIG. 6) that can be communicatively coupled to public Internet 954. Public Internet 954 can be communicatively coupled to the NAT gateway 938 contained in the control plane VCN 916 and contained in the data plane VCN 918. The service gateway 936 contained in the control plane VCN 916 and contained in the data plane VCN 918 can be communicatively coupled to cloud services 956.

In some examples, the pattern illustrated by the architecture of block diagram 900 of FIG. 9 may be considered an exception to the pattern illustrated by the architecture of block diagram 700 of FIG. 7 and may be desirable for a customer of the IaaS provider if the IaaS provider cannot directly communicate with the customer (e.g., a disconnected region). The respective containers 967(1)-(N) that are contained in the VMs 966(1)-(N) for each customer can be accessed in real-time by the customer. The containers 967(1)-(N) may be configured to make calls to respective secondary VNICs 972(1)-(N) contained in app subnet(s) 926 of the data plane app tier 946 that can be contained in the container egress VCN 968. The secondary VNICs 972(1)-(N) can transmit the calls to the NAT gateway 938 that may transmit the calls to public Internet 954. In this example, the containers 967(1)-(N) that can be accessed in real-time by the customer can be isolated from the control plane VCN 916 and can be isolated from other entities contained in the data plane VCN 918. The containers 967(1)-(N) may also be isolated from resources from other customers.

In other examples, the customer can use the containers 967(1)-(N) to call cloud services 956. In this example, the customer may run code in the containers 967(1)-(N) that requests a service from cloud services 956. The containers 967(1)-(N) can transmit this request to the secondary VNICs 972(1)-(N) that can transmit the request to the NAT gateway that can transmit the request to public Internet 954. Public Internet 954 can transmit the request to LB subnet(s) 922 contained in the control plane VCN 916 via the Internet gateway 934. In response to determining the request is valid, the LB subnet(s) can transmit the request to app subnet(s) 926 that can transmit the request to cloud services 956 via the service gateway 936.

It should be appreciated that IaaS architectures 600, 700, 800, 900 depicted in the figures may have other components than those depicted. Further, the embodiments shown in the figures are only some examples of a cloud infrastructure system that may incorporate an embodiment of the disclosure. In some other embodiments, the IaaS systems may have more or fewer components than shown in the figures, may combine two or more components, or may have a different configuration or arrangement of components.

In certain embodiments, the IaaS systems described herein may include a suite of applications, middleware, and database service offerings that are delivered to a customer in a self-service, subscription-based, elastically scalable, reliable, highly available, and secure manner. An example of such an IaaS system is the Oracle Cloud Infrastructure (OCI) provided by the present assignee.

Figure 10:
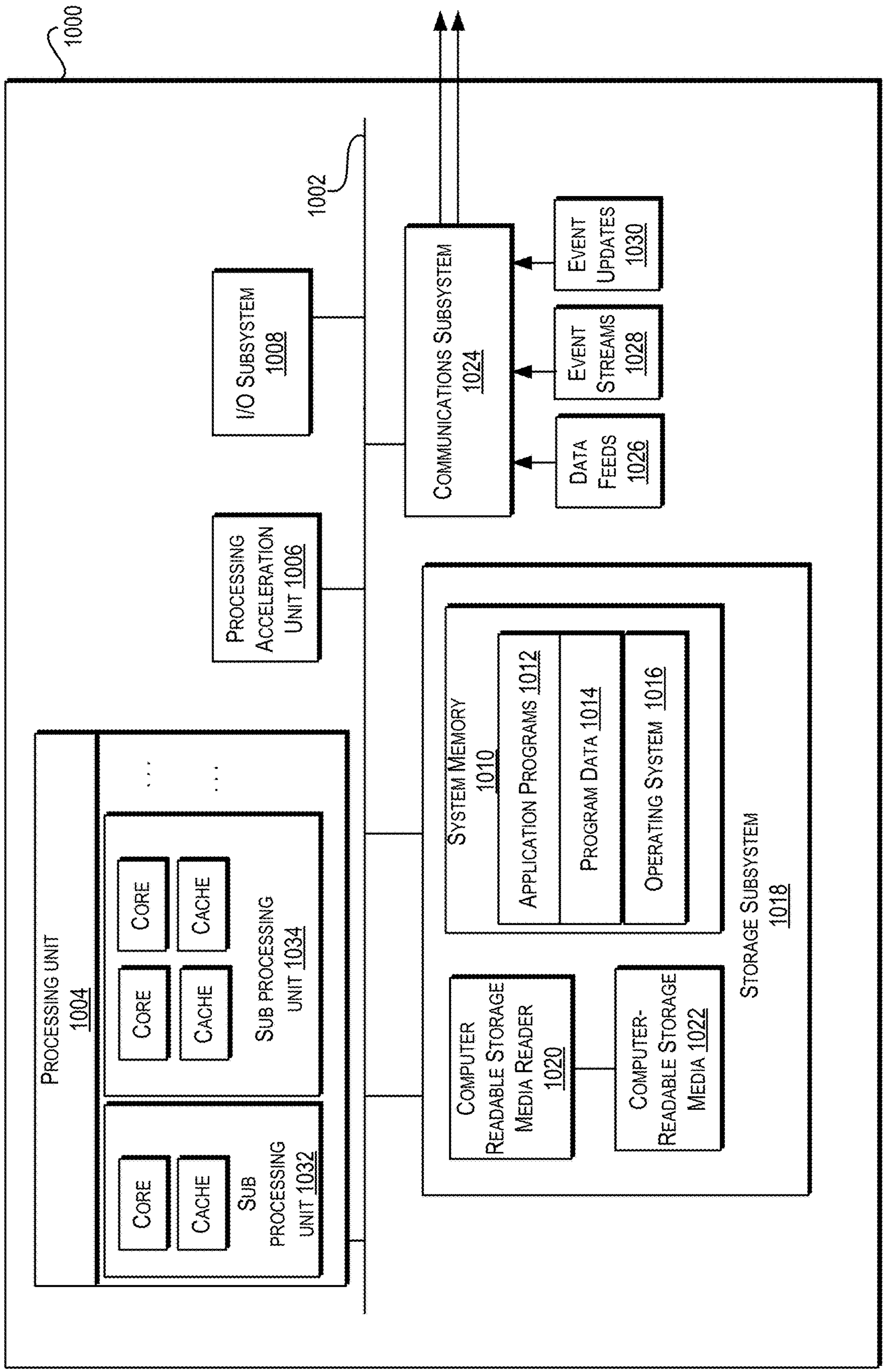
FIG. 10 is a block diagram illustrating an example computer system according to certain embodiments.

FIG. 10 illustrates an example computer system 1000, in which various embodiments may be implemented. The system 1000 may be used to implement any of the computer systems described above. As shown in the figure, computer system 1000 includes a processing unit 1004 that communicates with a number of peripheral subsystems via a bus subsystem 1002. These peripheral subsystems may include a processing acceleration unit 1006, an I/O subsystem 1008, a storage subsystem 1018 and a communications subsystem 1024. Storage subsystem 1018 includes tangible computer-readable storage media 1022 and a system memory 1010.

Bus subsystem 1002 provides a mechanism for letting the various components and subsystems of computer system 1000 communicate with each other as intended. Although bus subsystem 1002 is shown schematically as a single bus, alternative embodiments of the bus subsystem may utilize multiple buses. Bus subsystem 1002 may be any of several types of bus structures including a memory bus or memory controller, a peripheral bus, and a local bus using any of a variety of bus architectures. For example, such architectures may include an Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus, which can be implemented as a Mezzanine bus manufactured to the IEEE P1386.1 standard.

Processing unit 1004, which can be implemented as one or more integrated circuits (e.g., a conventional microprocessor or microcontroller), controls the operation of computer system 1000. One or more processors may be included in processing unit 1004. These processors may include single core or multicore processors. In certain embodiments, processing unit 1004 may be implemented as one or more independent processing units 1032 and/or 1034 with single or multicore processors included in each processing unit. In other embodiments, processing unit 1004 may also be implemented as a quad-core processing unit formed by integrating two dual-core processors into a single chip.

In various embodiments, processing unit 1004 can execute a variety of programs in response to program code and can maintain multiple concurrently executing programs or processes. At any given time, some, or all of the program code to be executed can be resident in processing unit 1004 and/or in storage subsystem 1018. Through suitable programming, processing unit 1004 can provide various functionalities described above. Computer system 1000 may additionally include a processing acceleration unit 1006, which can include a digital signal processor (DSP), a special-purpose processor, and/or the like.

I/O subsystem 1008 may include user interface input devices and user interface output devices. User interface input devices may include a keyboard, pointing devices such as a mouse or trackball, a touchpad or touch screen incorporated into a display, a scroll wheel, a click wheel, a dial, a button, a switch, a keypad, audio input devices with voice command recognition systems, microphones, and other types of input devices. User interface input devices may include, for example, motion sensing and/or gesture recognition devices such as the Microsoft Kinect® motion sensor that enables users to control and interact with an input device, such as the Microsoft Xbox® 360 game controller, through a natural user interface using gestures and spoken commands. User interface input devices may also include eye gesture recognition devices such as the Google Glass® blink detector that detects eye activity (e.g., 'blinking' while taking pictures and/or making a menu selection) from users and transforms the eye gestures as input into an input device (e.g., Google Glass®). Additionally, user interface input devices may include voice recognition sensing devices that enable users to interact with voice recognition systems (e.g., Siri® navigator), through voice commands.

User interface input devices may also include, without limitation, three dimensional (3D) mice, joysticks or pointing sticks, gamepads and graphic tablets, and audio/visual devices such as speakers, digital cameras, digital camcorders, portable media players, webcams, image scanners, fingerprint scanners, barcode reader 3D scanners, 3D printers, laser rangefinders, and eye gaze tracking devices. Additionally, user interface input devices may include, for example, medical imaging input devices such as computed tomography, magnetic resonance imaging, position emission tomography, medical ultrasonography devices. User interface input devices may also include, for example, audio input devices such as MIDI keyboards, digital musical instruments and the like.

User interface output devices may include a display subsystem, indicator lights, or non-visual displays such as audio output devices, etc. The display subsystem may be a cathode ray tube (CRT), a flat-panel device, such as that using a liquid crystal display (LCD) or plasma display, a projection device, a touch screen, and the like. In general, use of the term "output device" is intended to include all possible types of devices and mechanisms for outputting information from computer system 1000 to a user or other computer. For example, user interface output devices may include, without limitation, a variety of display devices that visually convey text, graphics, and audio/video information such as monitors, printers, speakers, headphones, automotive navigation systems, plotters, voice output devices, and modems.

Computer system 1000 may comprise a storage subsystem 1018 that provides a tangible non-transitory computer-readable storage medium for storing software and data constructs that provide the functionality of the embodiments described in this disclosure. The software can include programs, code modules, instructions, scripts, etc., that when executed by one or more cores or processors of processing unit 1004 provide the functionality described above. Storage subsystem 1018 may also provide a repository for storing data used in accordance with the present disclosure.

As depicted in the example in FIG. 10, storage subsystem 1018 can include various components including a system memory 1010, computer-readable storage media 1022, and a computer readable storage media reader 1020. System memory 1010 may store program instructions 1012 that are loadable and executable by processing unit 1004. System memory 1010 may also store data 1014 that is used during the execution of the instructions and/or data that is generated during the execution of the program instructions. Various different kinds of programs may be loaded into system memory 1010 including but not limited to client applications, Web browsers, mid-tier applications, relational database management systems (RDBMS), virtual machines, containers, etc.

System memory 1010 may also store an operating system 1016. Examples of operating system 1016 may include various versions of Microsoft Windows®, Apple Macintosh®, and/or Linux operating systems, a variety of commercially-available UNIX® or UNIX-like operating systems (including without limitation the variety of GNU/Linux operating systems, the Google Chrome® OS, and the like) and/or mobile operating systems such as iOS, Windows® Phone, Android® OS, BlackBerry® OS, and Palm® OS operating systems. In certain implementations where computer system 1000 executes one or more virtual machines, the virtual machines along with their guest operating systems (GOSs) may be loaded into system memory 1010 and executed by one or more processors or cores of processing unit 1004.

System memory 1010 can come in different configurations depending upon the type of computer system 1000. For example, system memory 1010 may be volatile memory (such as random access memory (RAM)) and/or non-volatile memory (such as read-only memory (ROM), flash memory, etc.) Different types of RAM configurations may be provided including a static random access memory (SRAM), a dynamic random access memory (DRAM), and others. In some implementations, system memory 1010 may include a basic input/output system (BIOS) containing basic routines that help to transfer information between elements within computer system 1000, such as during start-up.

Computer-readable storage media 1022 may represent remote, local, fixed, and/or removable storage devices plus storage media for temporarily and/or more permanently containing, storing, computer-readable information for use by computer system 1000 including instructions executable by processing unit 1004 of computer system 1000.

Computer-readable storage media 1022 can include any appropriate media known or used in the art, including storage media and communication media, such as but not limited to, volatile and non-volatile, removable, and non-removable media implemented in any method or technology for storage and/or transmission of information. This can include tangible computer-readable storage media such as RAM, ROM, electronically erasable programmable ROM (EEPROM), flash memory or other memory technology, CD-ROM, digital versatile disk (DVD), or other optical storage, magnetic cassettes, magnetic tape, magnetic disk storage or other magnetic storage devices, or other tangible computer readable media.

By way of example, computer-readable storage media 1022 may include a hard disk drive that reads from or writes to non-removable, nonvolatile magnetic media, a magnetic disk drive that reads from or writes to a removable, nonvolatile magnetic disk, and an optical disk drive that reads from or writes to a removable, nonvolatile optical disk such as a CD ROM, DVD, and Blu-Ray® disk, or other optical media. Computer-readable storage media 1022 may include, but is not limited to, Zip® drives, flash memory cards, universal serial bus (USB) flash drives, secure digital (SD) cards, DVD disks, digital video tape, and the like. Computer-readable storage media 1022 may also include, solid-state drives (SSD) based on non-volatile memory such as flash-memory based SSDs, enterprise flash drives, solid state ROM, and the like, SSDs based on volatile memory such as solid state RAM, dynamic RAM, static RAM, DRAM-based SSDs, magnetoresistive RAM (MRAM) SSDs, and hybrid SSDs that use a combination of DRAM and flash memory based SSDs. The disk drives and their associated computer-readable media may provide non-volatile storage of computer-readable instructions, data structures, program modules, and other data for computer system 1000.

Machine-readable instructions executable by one or more processors or cores of processing unit 1004 may be stored on a non-transitory computer-readable storage medium. A non-transitory computer-readable storage medium can include physically tangible memory or storage devices that include volatile memory storage devices and/or non-volatile storage devices. Examples of non-transitory computer-readable storage medium include magnetic storage media (e.g., disk or tapes), optical storage media (e.g., DVDs, CDs), various types of RAM, ROM, or flash memory, hard drives, floppy drives, detachable memory drives (e.g., USB drives), or other type of storage device.

Communications subsystem 1024 provides an interface to other computer systems and networks. Communications subsystem 1024 serves as an interface for receiving data from and transmitting data to other systems from computer system 1000. For example, communications subsystem 1024 may enable computer system 1000 to connect to one or more devices via the Internet. In some embodiments communications subsystem 1024 can include radio frequency (RF) transceiver components for accessing wireless voice and/or data networks (e.g., using cellular telephone technology, advanced data network technology, such as 3G, 4G or EDGE (enhanced data rates for global evolution), WiFi (IEEE 602.10 family standards, or other mobile communication technologies, or any combination thereof), global positioning system (GPS) receiver components, and/or other components. In some embodiments communications subsystem 1024 can provide wired network connectivity (e.g., Ethernet) in addition to or instead of a wireless interface.

In some embodiments, communications subsystem 1024 may also receive input communication in the form of structured and/or unstructured data feeds 1026, event streams 1028, event updates 1030, and the like on behalf of one or more users who may use computer system 1000.

By way of example, communications subsystem 1024 may be configured to receive data feeds 1026 in real-time from users of social networks and/or other communication services such as Twitter® feeds, Facebook® updates, web feeds such as Rich Site Summary (RSS) feeds, and/or real-time updates from one or more third party information sources.

Additionally, communications subsystem 1024 may also be configured to receive data in the form of continuous data streams, which may include event streams 1028 of real-time events and/or event updates 1030, that may be continuous or unbounded in nature with no explicit end. Examples of applications that generate continuous data may include, for example, sensor data applications, financial tickers, network performance measuring tools (e.g., network monitoring and traffic management applications), clickstream analysis tools, automobile traffic monitoring, and the like.

Communications subsystem 1024 may also be configured to output the structured and/or unstructured data feeds 1026, event streams 1028, event updates 1030, and the like to one or more databases that may be in communication with one or more streaming data source computers coupled to computer system 1000.

Computer system 1000 can be one of various types, including a handheld portable device (e.g., an iPhone® cellular phone, an iPad® computing tablet, a PDA), a wearable device (e.g., a Google Glass® head mounted display), a PC, a workstation, a mainframe, a kiosk, a server rack, or any other data processing system.

Due to the ever-changing nature of computers and networks, the description of computer system 1000 depicted in the figure is intended only as a specific example. Many other configurations having more or fewer components than the system depicted in the figure are possible. For example, customized hardware might also be used and/or particular elements might be implemented in hardware, firmware, software (including applets), or a combination. Further, connection to other computing devices, such as network input/output devices, may be employed. Based on the disclosure and teachings provided herein, a person of ordinary skill in the art will appreciate other ways and/or methods to implement the various embodiments.

Although specific embodiments have been described, various modifications, alterations, alternative constructions, and equivalents are also encompassed within the scope of the disclosure. Embodiments are not restricted to operation within certain specific data processing environments but are free to operate within a plurality of data processing environments. Additionally, although embodiments have been described using a particular series of transactions and steps, it should be apparent to those skilled in the art that the scope of the present disclosure is not limited to the described series of transactions and steps. Various features and aspects of the above-described embodiments may be used individually or jointly.

Further, while embodiments have been described using a particular combination of hardware and software, it should be recognized that other combinations of hardware and software are also within the scope of the present disclosure. Embodiments may be implemented only in hardware, or only in software, or using combinations thereof. The various processes described herein can be implemented on the same processor or different processors in any combination. Accordingly, where components or services are described as being configured to perform certain operations, such configuration can be accomplished, e.g., by designing electronic circuits to perform the operation, by programming programmable electronic circuits (such as microprocessors) to perform the operation, or any combination thereof. Processes can communicate using a variety of techniques including but not limited to conventional techniques for inter process communication, and different pairs of processes may use different techniques, or the same pair of processes may use different techniques at different times.

The specification and drawings are, accordingly, to be regarded in an illustrative rather than a restrictive sense. It will, however, be evident that additions, subtractions, deletions, and other modifications and changes may be made thereunto without departing from the broader spirit and scope as set forth in the claims. Thus, although specific disclosure embodiments have been described, these are not intended to be limiting. Various modifications and equivalents are within the scope of the following claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments and does not pose a limitation on the scope of the disclosure unless otherwise claimed. No language in the specification should be construed as indicating any non-claimed element as essential to the practice of the disclosure.

As used herein, when an action is "based on" something, this means the action is based at least in part on at least a part of the something. As used herein, the terms "substantially," "approximately" and "about" are defined as being largely but not necessarily wholly what is specified (and include wholly what is specified) as understood by one of ordinary skill in the art. In any disclosed embodiment, the term "substantially," "approximately," or "about" may be substituted with "within [a percentage] of" what is specified, where the percentage includes 0.1, 1, 6, and 8 percent.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Preferred embodiments of this disclosure are described herein, including the best mode known for carrying out the disclosure. Variations of those preferred embodiments may become apparent to those of ordinary skill in the art upon reading the foregoing description. Those of ordinary skill should be able to employ such variations as appropriate and the disclosure may be practiced otherwise than as specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein.

All references, including publications, patent applications, and patents, cited herein are hereby incorporated by reference to the same extent as if each reference were individually and specifically indicated to be incorporated by reference and were set forth in its entirety herein.

In the foregoing specification, aspects of the disclosure are described with reference to specific embodiments thereof, but those skilled in the art will recognize that the disclosure is not limited thereto. Various features and aspects of the above-described disclosure may be used individually or jointly. Further, embodiments can be utilized in any number of environments and applications beyond those described herein without departing from the broader spirit and scope of the specification. The specification and drawings are, accordingly, to be regarded as illustrative rather than restrictive.

What is claimed is:

1. A computer-implemented method comprising:

accessing a text transcript, the text transcript corresponding to an interaction between a first entity and a second entity;

segmenting the text transcript into a plurality of text segments, wherein segmenting the text transcript comprises, for a respective text segment that comprises a question, adding a subsequent turn from the text transcript that answers that question;

for each respective text segment of the plurality of text segments:

identifying a set of entities that are included in the respective text segment, wherein identifying the set of entities that are included in the respective text segment comprises:

using a first machine-learning model to extract a plurality of first entities included in the respective text segment, using a second machine-learning model, different from the first machine-learning model, to extract a plurality of second entities included in the respective text segment, and processing the plurality of first entities and the plurality of second entities to identify the set of entities, wherein processing the plurality of first entities and the plurality of second entities comprises removing a first entity from the plurality of first entities that is included in the plurality of second entities;

generating a Subjective, Objective, Assessment, and Plan (SOAP) note using a third machine-learning model based at least in-part on the set of entities; and storing the SOAP note in a database associated with at least one of the first entity and the second entity.

2. The computer-implemented method of claim 1, wherein processing the plurality of first entities and the plurality of second entities further comprises removing a second entity of the plurality of second entities that is included in the plurality of first entities.

3. The computer-implemented method of claim 1, wherein processing the plurality of first entities and the plurality of second entities comprises comparing the plurality of second entities to the respective text segment to determine whether each second entity in the plurality of second entities is included in the respective text segment, and discarding any second entities in the plurality of second entities that are not included in the respective text segment.

4. The computer-implemented method of claim 1, wherein processing the plurality of first entities and the plurality of second entities further comprises processing the set of entities to remove additional instances of any entity that is included in the set of entities more than once such that the set of entities includes a single instance of each entity.

5. The computer-implemented method of claim 1, wherein the first machine-learning model is a named entity recognition model that is configured to recognize named entities in input text, wherein the second machine-learning model is a pre-trained language model that is configured to generate a result in response to an input prompt, and wherein the third machine-learning model is a pre-trained language model that is configured to generate a result in response to an input prompt.

6. The computer-implemented method of claim 1, further comprising:

for each respective text segment of the plurality of text segments:

using a fourth machine-learning model to extract one or more facts from the respective text segment based at least in-part on the set of entities, and adding the one or more facts to a collection of facts; and generating a set of classified facts from the collection of facts, wherein each classified fact of the set of classified facts corresponds to a fact in the collection of facts and is associated with a particular category label selected from a set of category labels.

7. The computer-implemented method of claim 6, wherein generating the SOAP note using the third machine-learning model based at least in-part on the set of entities comprises using the third machine-learning model to generate a set of note sections based at least in-part on the set of classified facts, wherein each note section of the set of note sections corresponds to a section of the SOAP note.

8. A system comprising:

one or more processing systems; and one or more computer-readable media storing instructions which, when executed by the one or more processing systems, cause the system to perform operations comprising:

accessing a text transcript, the text transcript corresponding to an interaction between a first entity and a second entity;

segmenting the text transcript into a plurality of text segments, wherein segmenting the text transcript comprises, for a respective text segment that comprises a question, adding a subsequent turn from the text transcript that answers that question;

for each respective text segment of the plurality of text segments:

identifying a set of entities that are included in the respective text segment, wherein identifying the set of entities that are included in the respective text segment comprises:

using a first machine-learning model to extract a plurality of first entities included in the respective text segment, using a second machine-learning model, different from the first machine-learning model, to extract a plurality of second entities included in the respective text segment, and processing the plurality of first entities and the plurality of second entities to identify the set of entities, wherein processing the plurality of first entities and the plurality of second entities comprises removing a first entity from the plurality of first entities that is included in the plurality of second entities;

generating a Subjective, Objective, Assessment, and Plan (SOAP) note using a third machine-learning model based at least in-part on the set of entities; and storing the SOAP note in a database associated with at least one of the first entity and the second entity.

9. The system of claim 8, wherein processing the plurality of first entities and the plurality of second entities further comprises removing a second entity of the plurality of second entities that is included in the plurality of first entities.

10. The system of claim 8, wherein processing the plurality of first entities and the plurality of second entities comprises comparing the plurality of second entities to the respective text segment to determine whether each second entity in the plurality of second entities is included in the respective text segment, and discarding any second entities in the plurality of second entities that are not included in the respective text segment.

11. The system of claim 8, wherein processing the plurality of first entities and the plurality of second entities further comprises processing the set of entities to remove additional instances of any entity that is included in the set of entities more than once such that the set of entities includes a single instance of each entity.

12. The system of claim 8, wherein the first machine-learning model is a named entity recognition model that is configured to recognize named entities in input text, wherein the second machine-learning model is a pre-trained language model that is configured to generate a result in response to an input prompt, and wherein the third machine-learning model is a pre-trained language model that is configured to generate a result in response to an input prompt.

13. The system of claim 8, the operations further comprising:

for each respective text segment of the plurality of text segments:

using a fourth machine-learning model to extract one or more facts from the respective text segment based at least in-part on the set of entities, and adding the one or more facts to a collection of facts; and generating a set of classified facts from the collection of facts, wherein each classified fact of the set of classified facts corresponds to a fact in the collection of facts and is associated with a particular category label selected from a set of category labels.

14. The system of claim 13, wherein generating the SOAP note using the third machine-learning model based at least in-part on the set of entities comprises using the third machine-learning model to generate a set of note sections based at least in-part on the set of classified facts, wherein each note section of the set of note sections corresponds to a section of the SOAP note.

15. One or more non-transitory computer-readable media storing instructions which, when executed by one or more processors, cause a system to perform operations comprising:

accessing a text transcript, the text transcript corresponding to an interaction between a first entity and a second entity;

segmenting the text transcript into a plurality of text segments, wherein segmenting the text transcript comprises, for a respective text segment that comprises a question, adding a subsequent turn from the text transcript that answers that question;

for each respective text segment of the plurality of text segments:

identifying a set of entities that are included in the respective text segment, wherein identifying the set of entities that are included in the respective text segment comprises:

using a first machine-learning model to extract a plurality of first entities included in the respective text segment, using a second machine-learning model, different from the first machine-learning model, to extract a plurality of second entities included in the respective text segment, and processing the plurality of first entities and the plurality of second entities to identify the set of entities, wherein processing the plurality of first entities and the plurality of second entities comprises removing a first entity from the plurality of first entities that is included in the plurality of second entities;

generating a Subjective, Objective, Assessment, and Plan (SOAP) note using a third machine-learning model based at least in-part on the set of entities; and storing the SOAP note in a database associated with at least one of the first entity and the second entity.

16. The one or more non-transitory computer-readable media of claim 15, wherein processing the plurality of first entities and the plurality of second entities further comprises removing a second entity of the plurality of second entities that is included in the plurality of first entities.

17. The one or more non-transitory computer-readable media of claim 15, wherein processing the plurality of first entities and the plurality of second entities comprises comparing the plurality of second entities to the respective text segment to determine whether each second entity in the plurality of second entities is included in the respective text segment, and discarding any second entities in the plurality of second entities that are not included in the respective text segment.

18. The one or more non-transitory computer-readable media of claim 15, wherein processing the plurality of first entities and the plurality of second entities further comprises processing the set of entities to remove additional instances of any entity that is included in the set of entities more than once such that the set of entities includes a single instance of each entity.

19. The one or more non-transitory computer-readable media of claim 15, wherein the first machine-learning model is a named entity recognition model that is configured to recognize named entities in input text, wherein the second machine-learning model is a pre-trained language model that is configured to generate a result in response to an input prompt, and wherein the third machine-learning model is a pre-trained language model that is configured to generate a result in response to an input prompt.

20. The one or more non-transitory computer-readable media of claim 15, the operations further comprising:

for each respective text segment of the plurality of text segments:

using a fourth machine-learning model to extract one or more facts from the respective text segment based at least in-part on the set of entities, and adding the one or more facts to a collection of facts; and generating a set of classified facts from the collection of facts, wherein each classified fact of the set of classified facts corresponds to a fact in the collection of facts and is associated with a particular category label selected from a set of category labels, wherein generating the SOAP note using the third machine-learning model based at least in-part on the set of entities comprises using the third machine-learning model to generate a set of note sections based at least in-part on the set of classified facts, wherein each note section of the set of note sections corresponds to a section of the SOAP note.

* * * * *